United States Patent
Cowens et al.

(10) Patent No.: US 10,722,269 B2
(45) Date of Patent: Jul. 28, 2020

(54) VARIABLE-ANGLE BONE PLATE PLACEMENT TOOL, SYSTEM, AND METHOD OF USING THE SAME

(71) Applicant: DePuy Synthes Products, Inc., Raynham, MA (US)

(72) Inventors: David Cowens, West Chester, PA (US); Alexandra Sibole, West Chester, PA (US)

(73) Assignee: DePuy Synthes Products, Inc.

( * ) Notice: Subject to any disclaimer, the term of this patent is extended or adjusted under 35 U.S.C. 154(b) by 299 days.

(21) Appl. No.: 15/638,471

(22) Filed: Jun. 30, 2017

(65) Prior Publication Data
US 2019/0000509 A1   Jan. 3, 2019

(51) Int. Cl.
*A61B 17/68* (2006.01)
*A61B 17/17* (2006.01)
*A61B 17/86* (2006.01)
*A61B 17/80* (2006.01)
*A61B 90/00* (2016.01)

(52) U.S. Cl.
CPC .......... *A61B 17/68* (2013.01); *A61B 17/1725* (2013.01); *A61B 17/1728* (2013.01); *A61B 17/808* (2013.01); *A61B 17/8061* (2013.01); *A61B 17/8605* (2013.01); *A61B 17/8057* (2013.01); *A61B 2090/067* (2016.02)

(58) Field of Classification Search
CPC . A61B 17/68; A61B 17/1725; A61B 17/1753; A61B 17/1742; A61B 17/1717; A61B 17/1728; A61B 17/8061; A61B 17/808
See application file for complete search history.

(56) References Cited

U.S. PATENT DOCUMENTS

| | | | |
|---|---|---|---|
| 6,066,142 A | 5/2000 | Serbousek et al. | |
| 6,830,574 B2 | 12/2004 | Heckele et al. | |
| 7,572,276 B2 | 8/2009 | Lim et al. | |
| 7,648,506 B2 | 1/2010 | McCord et al. | |
| 7,708,743 B2 | 5/2010 | Anderson et al. | |
| 7,935,123 B2 | 5/2011 | Fanger et al. | |
| 8,834,484 B2 * | 9/2014 | Kehres | A61B 17/00 606/104 |
| 9,095,385 B2 | 8/2015 | Wallenstein et al. | |
| 2003/0040748 A1 * | 2/2003 | Aikins | A61B 17/1668 606/70 |
| 2013/0079829 A1 * | 3/2013 | Globerman | A61B 17/8033 606/286 |

(Continued)

*Primary Examiner* — Matthew J Lawson
(74) *Attorney, Agent, or Firm* — Wayne C. Jaeschke, Jr.

(57) ABSTRACT

In one embodiment, a bone-plate placement tool guides a bone plate against an outer surface of a bone so that the bone plate can be fastened to an intramedullary nail received in a medullary canal of the bone. The tool includes a guide shaft and a plate holder. The shaft defines a bore extending therethrough along an axis. The plate holder couples to a bone plate, and is coupled to the guide shaft such that the plate holder angulates relative to the axis along a range of angles. The bore of the shaft and a bore of the plate holder combine to define a passageway that extends through the tool as the plate holder angulates relative to the axis along the range of angles so as to guide at least one of a drill bit and a bone anchor through the tool and into an aperture in the bone plate.

15 Claims, 14 Drawing Sheets

(56) References Cited

U.S. PATENT DOCUMENTS

| | | | |
|---|---|---|---|
| 2013/0172890 A1* | 7/2013 | Limouze | A61B 17/1725 606/62 |
| 2015/0100094 A1* | 4/2015 | Milz | A61B 17/7059 606/280 |
| 2015/0359580 A1* | 12/2015 | Dacosta | A61B 17/17 606/281 |
| 2016/0206356 A1 | 7/2016 | Koey et al. | |
| 2018/0078290 A1* | 3/2018 | Rossney | A61B 17/72 |
| 2019/0269418 A1* | 9/2019 | Nino | A61B 17/1728 |

* cited by examiner

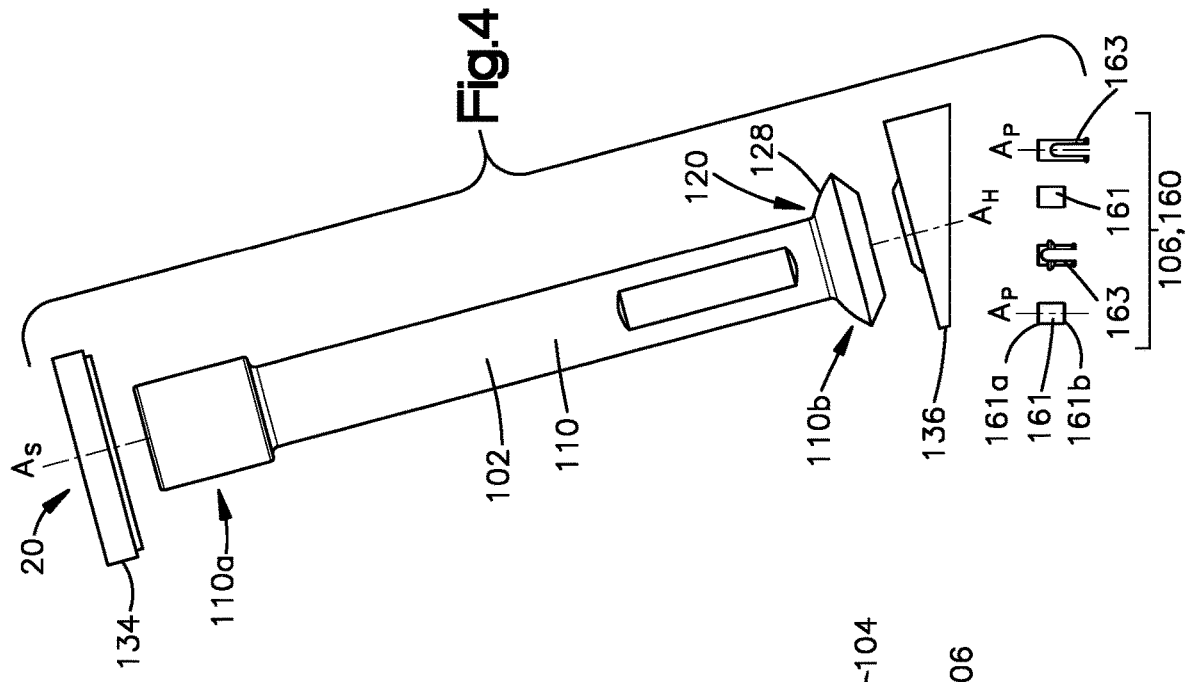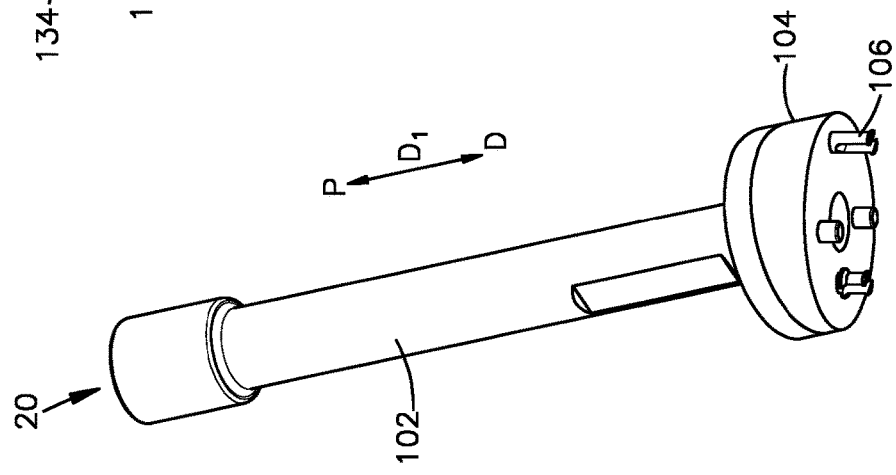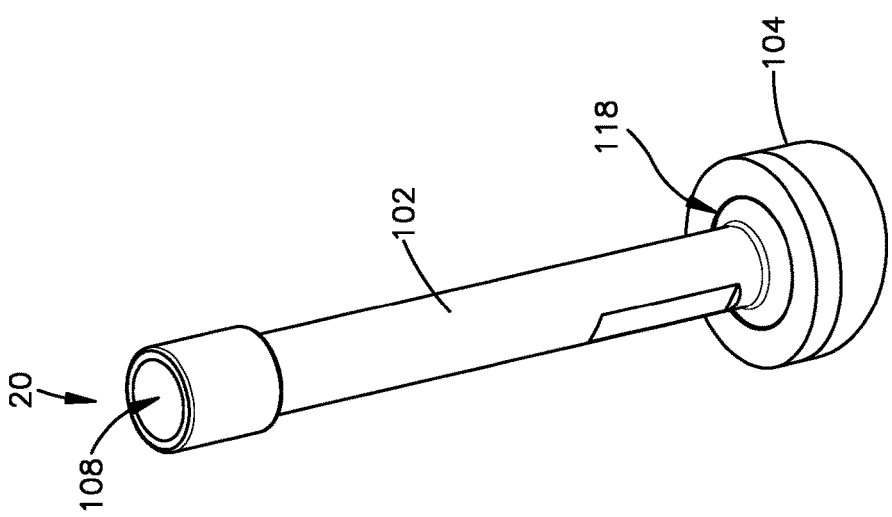

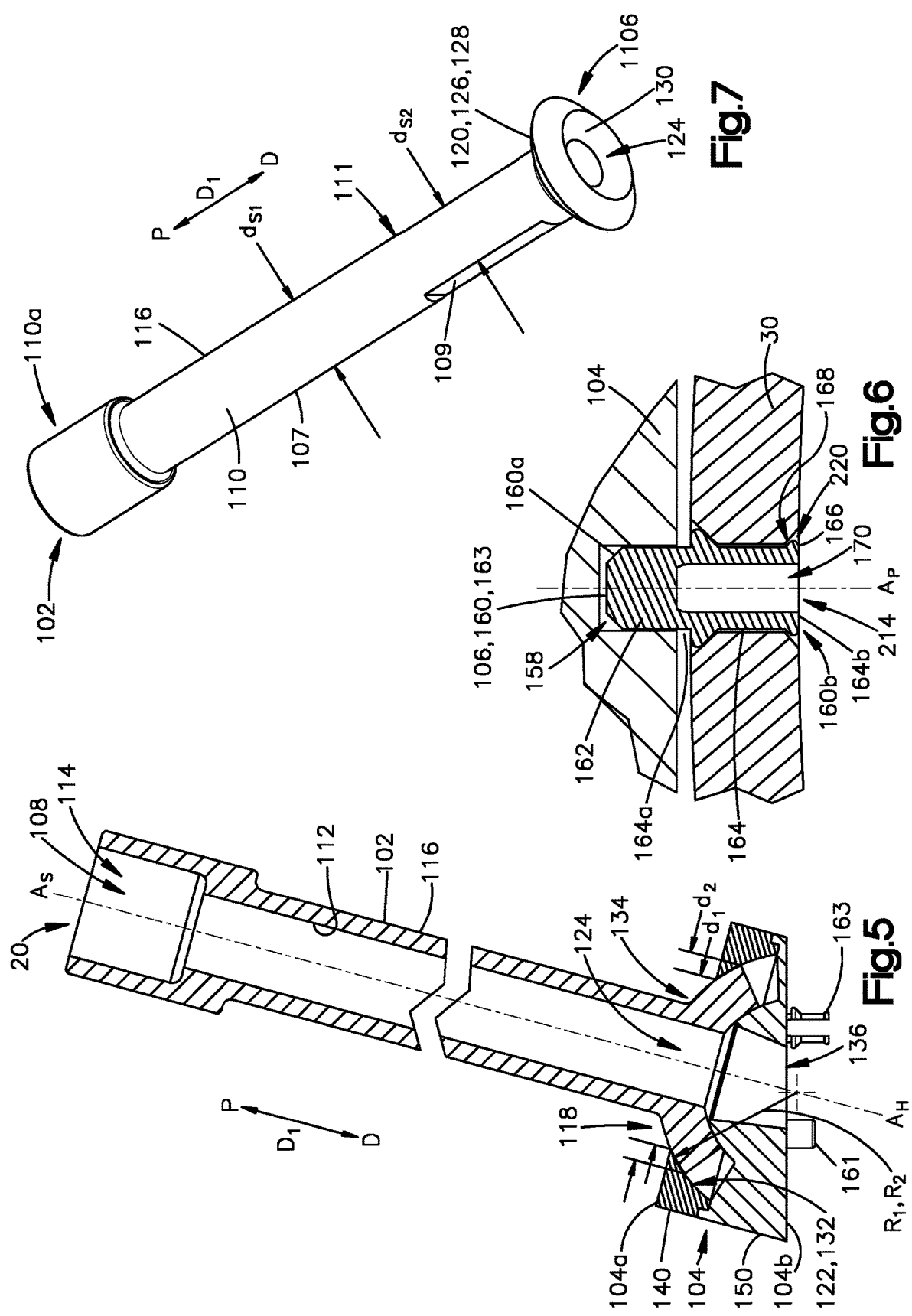

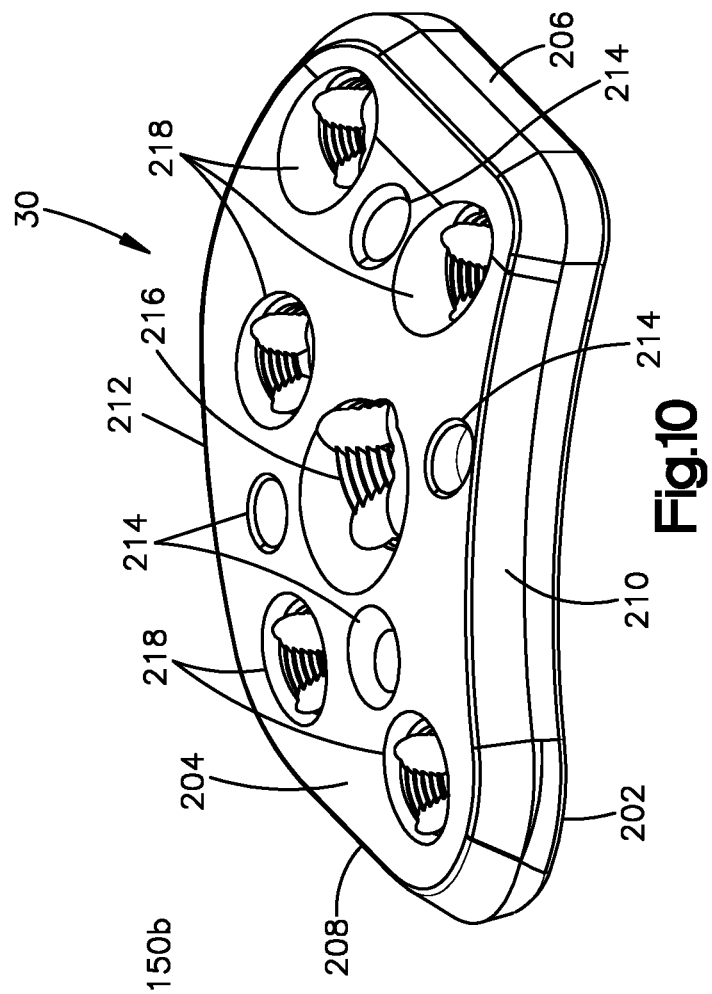
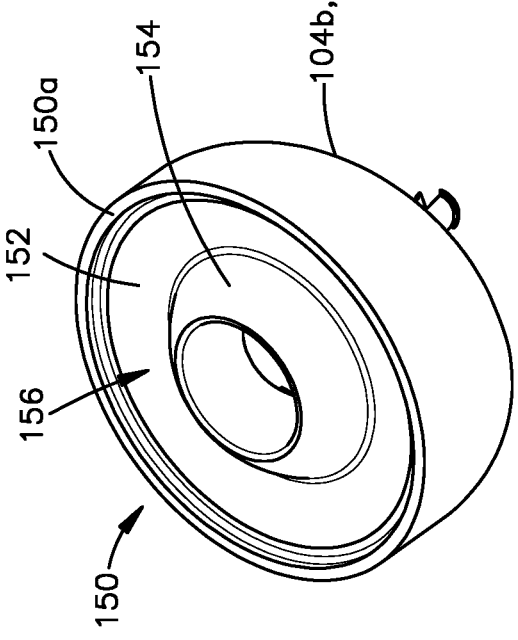
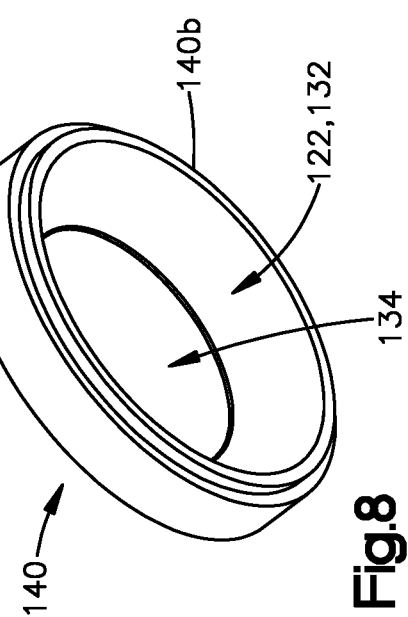

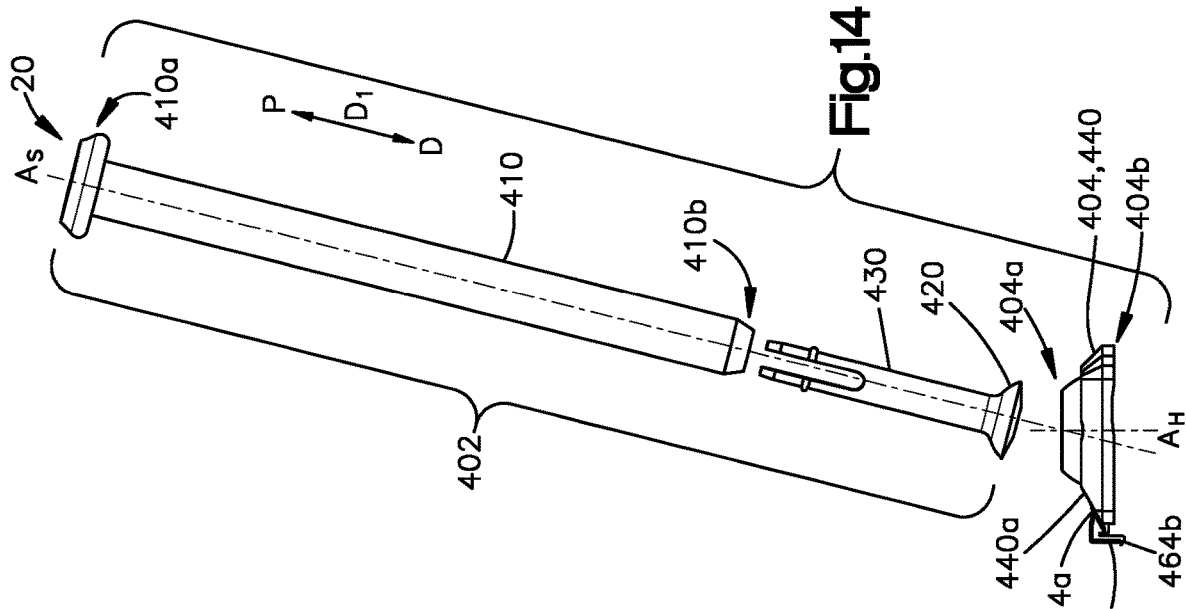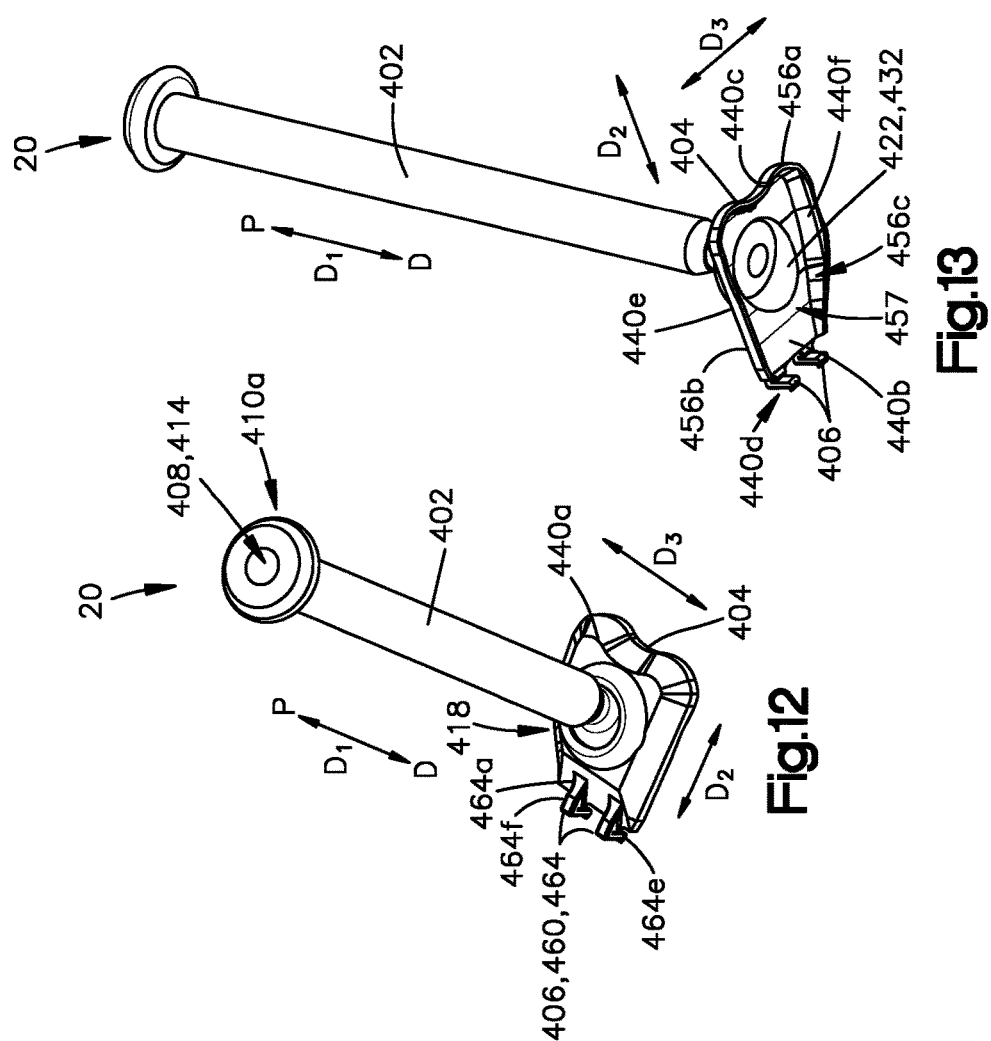

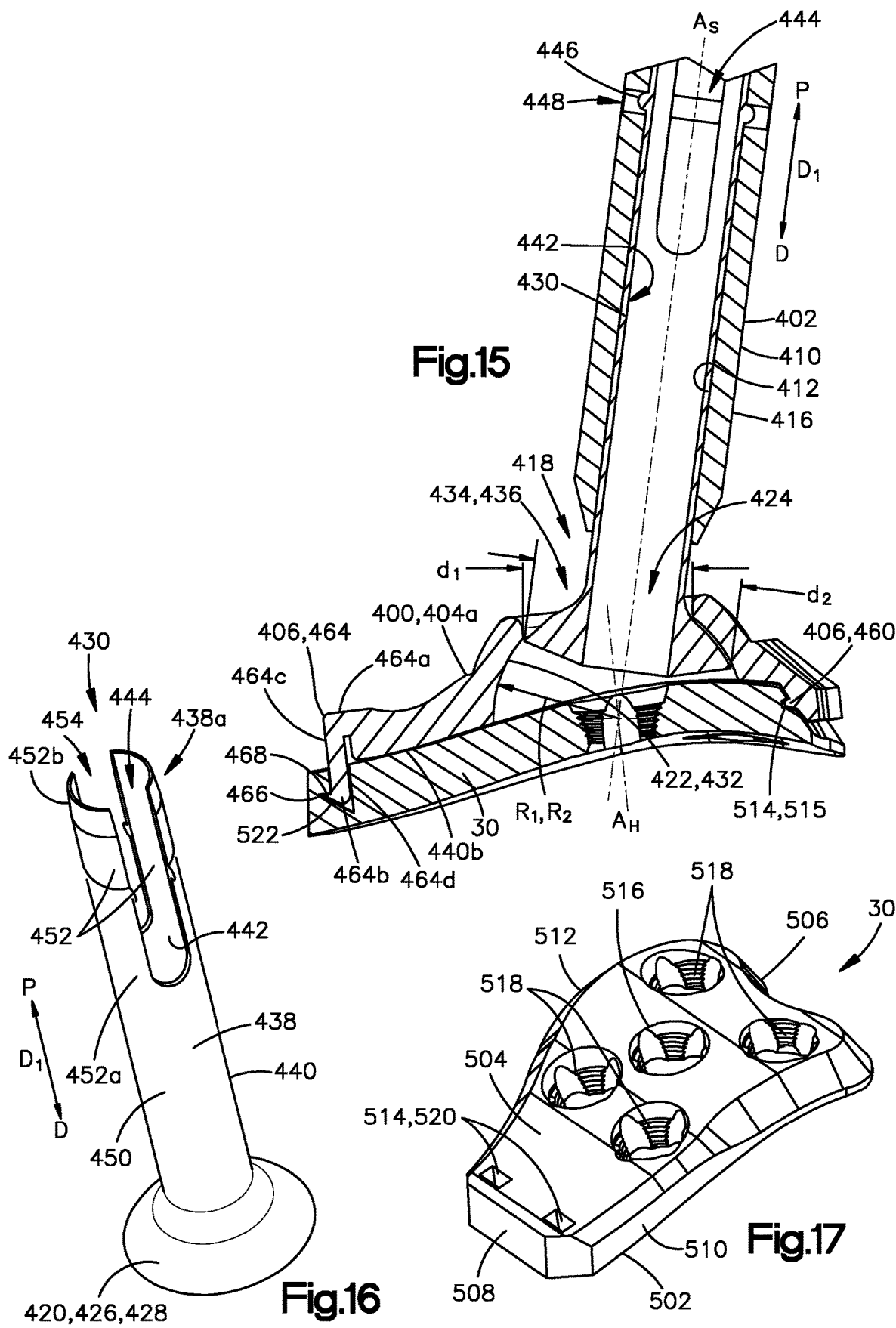

VARIABLE-ANGLE BONE PLATE PLACEMENT TOOL, SYSTEM, AND METHOD OF USING THE SAME

TECHNICAL FIELD

The present disclosure relates to systems, kits, assemblies, and methods for the placement and fixation of a bone plate against a bone for attachment to an intramedullary nail in a medullary canal of the bone.

BACKGROUND

Intramedullary nails have long been used to treat fractures in long bones of the body such as fractures in femurs, tibias, and humeri. To treat such fractures, the intramedullary nail is inserted into a medullary canal of the long bone such that the nail extends spans across one or more fractures in the long bone to segments of the long bone that are separated by the one or more fractures. Bone anchors are then inserted through the bone and into the intramedullary nail on opposing sides of the fracture, thereby fixing the intramedullary nail to the bone. The intramedullary nail can remain in the medullary canal at least until the fracture is fused.

SUMMARY

In an example embodiment, a bone-plate placement tool comprises a guide shaft and a plate holder. The guide shaft defines a bore extending therethrough along a shaft longitudinal axis. The plate holder is configured to releasably couple to a bone plate and defines a bore extending therethrough. Further, the plate holder is coupled to the guide shaft such that the plate holder is configured to angulate relative to the shaft longitudinal axis along a range of angles. The bores of the guide shaft and the plate holder combine to define a passageway that extends through the bone-plate placement tool as the plate holder angulates with respect to the shaft longitudinal axis along the range of angles. The passageway is configured to guide at least one of a drill bit and a bone anchor through the bone-plate placement tool and into an aperture in the bone plate when the plate holder is coupled to the bone plate.

In another example embodiment, a bone-plate placement system comprises a bone-plate placement tool similar to that described above, and an aiming assembly. The guide shaft of the bone-plate placement tool defines a bore that extends therethrough along a shaft longitudinal axis. The aiming assembly is configured to support the bone-plate placement tool such that, when the aiming assembly is coupled to an intramedullary nail, the aiming assembly aligns the shaft longitudinal axis of the bore with a bone-anchor aperture that extends into an intramedullary nail attached to the aiming assembly such that the bore is configured to receive at least one of a drill bit and a bone anchor through the bore and towards the bone-anchor aperture of the intramedullary nail.

In yet another example embodiment, a bone-plate placement system comprises a bone-plate placement tool similar to that described above, and a bone plate. The guide shaft of the bone-plate placement tool defines a bore that extends therethrough along a shaft longitudinal axis. The bone plate defines a bone-anchor aperture that extends therethrough such that, when the bone plate is fastened to the plate holder, the shaft longitudinal axis of the bore aligns with the bone-anchor aperture so as to receive at least one of a drill bit and a bone anchor through the bore and into the bone-anchor aperture.

In yet still another example embodiment, a method of attaching a bone plate to an intramedullary nail disposed in a medullary canal of a bone comprises fastening the bone plate to a plate holder of a bone-plate placement tool such that the bone plate is configured to angulate with the plate holder relative to a guide shaft of the bone-plate placement tool. The method further comprises advancing the bone-plate placement tool towards an outer surface of the bone until the bone plate contacts the outer surface of the bone causing the bone plate to angulate into alignment against the outer surface of the bone. The method yet further comprises securing the bone plate to the intramedullary nail by advancing at least one of a drill bit and a bone anchor through a passageway that extends through the guide shaft and the plate holder, and further through a bone-anchor aperture in the bone plate and into the bone towards the intramedullary nail.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 2 shows a perspective proximal-end view of the variable-angle bone-plate placement tool of FIG. 1 according to one embodiment;

FIG. 3 shows a perspective distal-end view of the variable-angle bone-plate placement tool of FIG. 2;

FIG. 4 shows an exploded side view of the variable-angle bone-plate placement tool of FIG. 2;

FIG. 5 shows a cross-sectional side view of the variable-angle bone-plate placement tool of FIG. 2;

FIG. 6 shows an enlarged cross-sectional side view of a fastener attaching the bone plate and the variable-angle bone-plate placement tool of FIG. 2 to one another;

FIG. 7 shows a perspective distal-end view of a guide shaft of the variable-angle bone-plate placement tool of FIG. 2;

FIG. 8 shows a perspective distal-end view a first plate of the plate holder of the variable-angle bone-plate placement tool of FIG. 2;

FIG. 9 shows a perspective proximal-end view of a second plate of the variable-angle bone-plate placement tool of FIG. 2;

FIG. 10 shows a perspective proximal-end view of the bone plate of FIG. 1 according to one embodiment;

FIG. 12 shows a perspective proximal-end view of the variable-angle bone-plate placement tool of FIG. 11 according to another embodiment;

FIG. 13 shows a perspective distal-end view of the variable-angle bone-plate placement tool of FIG. 12;

FIG. 14 shows an exploded side view of the variable-angle bone-plate placement tool of FIG. 12;

FIG. 15 shows a cross-sectional side view of the variable-angle bone-plate placement tool of FIG. 12 secured to a bone plate;

FIG. 16 shows a perspective proximal-end view of a bearing stud of the variable-angle bone-plate placement tool of FIG. 12;

FIG. 17 shows a perspective proximal-end view of the bone plate of FIG. 11 according to one embodiment;

DETAILED DESCRIPTION OF ILLUSTRATIVE EMBODIMENTS

An intramedullary nail is commonly secured to bone via at least one bone anchor, where each bone anchor extends directly into the surface of the bone and into a corresponding bone-anchor aperture in the intramedullary nail such that the bone anchor attaches to both the bone and the nail. However, as forces are exerted on the intramedullary nail, the attachment or bond between the bone anchor and the bone can weaken. This is especially true for patients whose bone at the bone anchor site is weakened due to osteoporosis or other bone conditions. To strengthen the attachment between the bone anchor and the bone, the bone anchor can be further secured to a bone plate that is positioned against the outer surface of the bone and that is further secured to the bone via one or more additional bone anchors. For example, the bone plate can be positioned against the bone, and a first bone anchor can be inserted into an aperture in the plate, through the surface of the bone, and into the intramedullary nail, such that the first bone anchor attaches to the plate, the bone, and the intramedullary nail. Further, one or more other bone anchors can be inserted into the plate adjacent the first bone anchor such that the one or more other bone anchors terminate in the bone with or without passing into the intramedullary nail. The one or more other bone anchors provide additional fixation to the bone that can reduce loading on the first bone anchor.

Figure 1:
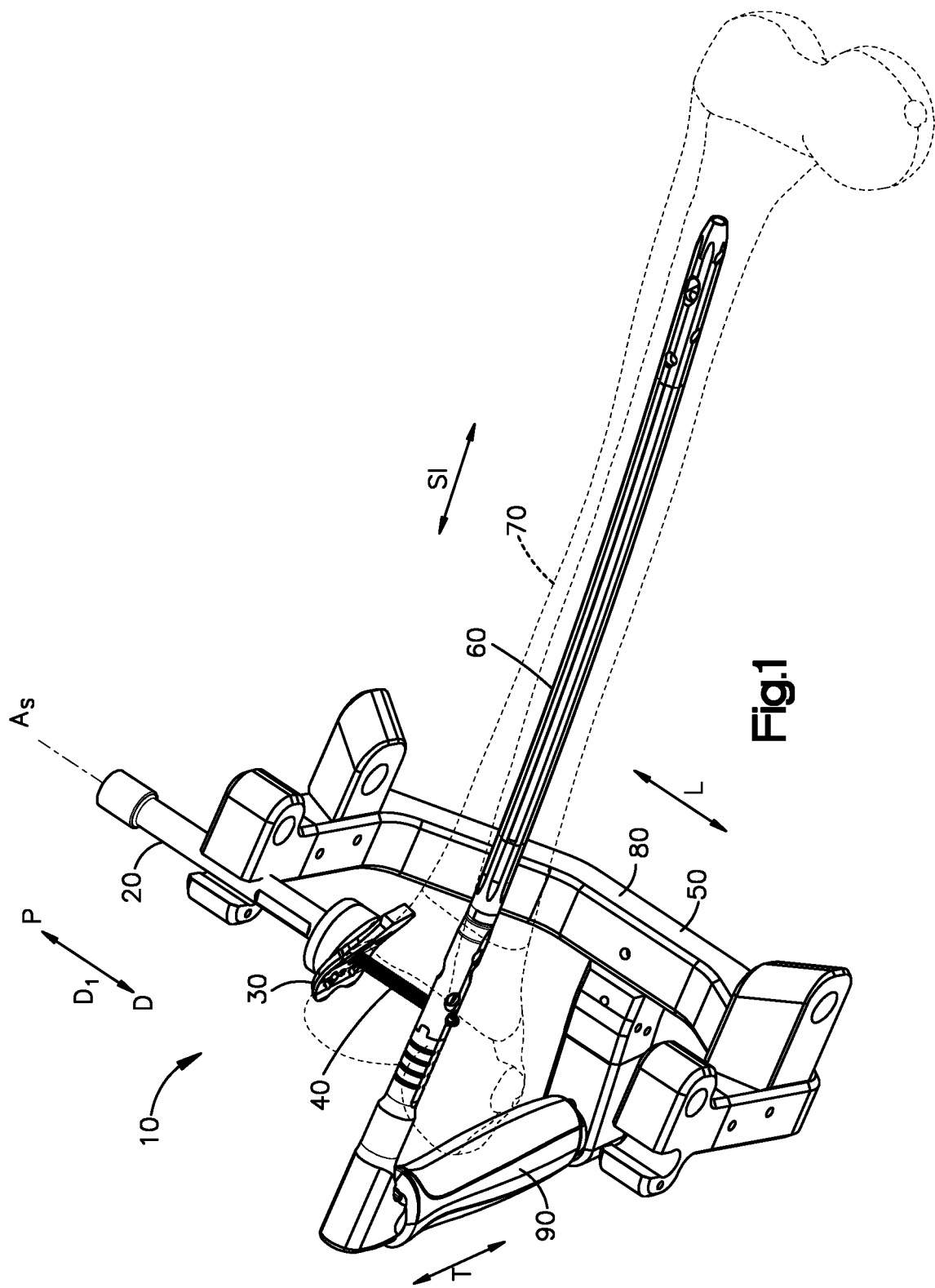
FIG. 1 shows a perspective view of a system according to one embodiment having a variable-angle bone-plate placement tool supported by an aiming assembly that is attached to an intramedullary nail received in a medullary canal of a bone.
Figure 11:
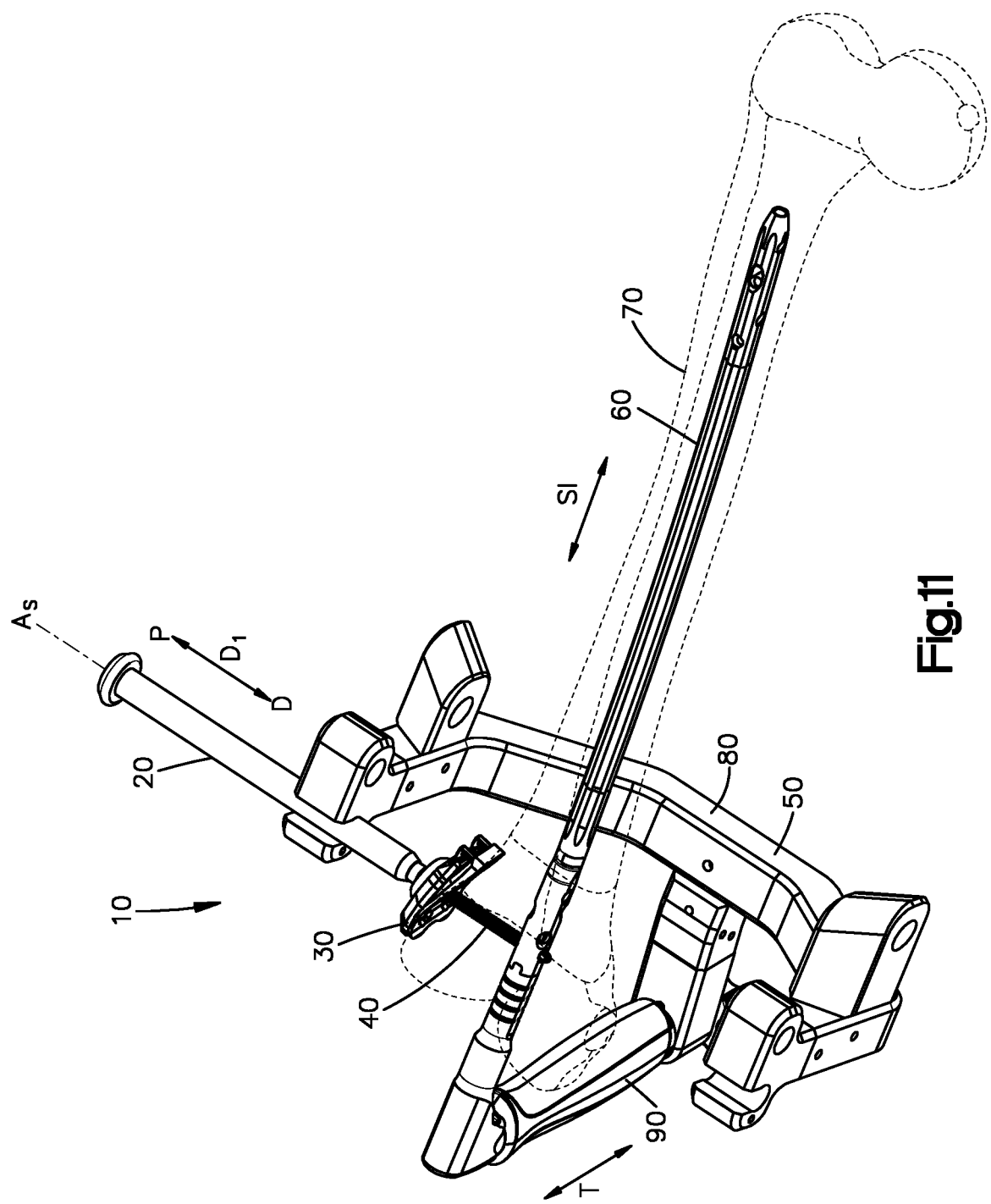
FIG. 11 shows a perspective view of a system according to another embodiment having a variable angle plate placement tool supported by an aiming assembly that is attached to an intramedullary nail received in a medullary canal of a bone.

Referring to FIGS. 1 and 11, example systems 10 are shown that are configured to position a bone plate 30 against a surface of a bone 70 as the bone plate 30 is fastened to the bone 70 and an intramedullary nail 60. In general, each system 10 comprises a variable-angle bone-plate placement tool 20 that supports the bone plate 30 and angulates the bone plate 30 so as to align a surface of the bone plate 30 with a surface of the bone 70. As will be described in further detail below, the bone-plate placement tool 20 of FIG. 1 is configured in accordance with the embodiment of FIGS. 2-9, and the bone-plate placement tool 20 of FIG. 11 is configured in accordance with the embodiment of FIGS. 12-16. However, it will be understood that alternative embodiments can be envisioned within the scope of this disclosure.

Each system 10 can further comprise one or more of the bone plate 30, at least one bone anchor 40 such as a bone screw, an aiming assembly 50, and an intramedullary nail 60. The intramedullary nail 60 is elongate generally along a superior-inferior direction SI and is sized to be received in a medullary canal of a long bone such as a femur, tibia, or humerus. The aiming assembly 50 releasably attaches to a proximal end of the intramedullary nail 30 and can comprise an aiming guide 80 and a handle 90. The aiming assembly 50 supports the bone-plate placement tool 20 at a location that is spaced from the intramedullary nail 60 along a first direction $D_1$ such that an axis $A_S$ of the bone-plate placement tool 20 is radially aligned with the intramedullary nail 60. For example, the axis $A_S$ of the bone-plate placement tool 20 can be aligned with a bone-anchor opening that extends radially through the intramedullary nail 60.

Referring to FIGS. 2-5, the bone-plate placement tool 20 of FIG. 1 comprises a guide shaft 102, a plate holder 104, and at least one bone-plate fastener 106. The plate holder 104 is coupled to the guide shaft 102 such that the plate holder 104 is configured to angulate relative to the guide shaft 102. In at least some embodiments, the plate holder 104 can angulate polyaxially relative to the guide shaft 102, although embodiments of the disclosure are not so limited. The at least one bone-plate fastener 106 is configured to releasably fasten the bone plate 30 to the plate holder 104 such that the bone plate 30 is positionally fixed relative to the plate holder 104 and is configured to angulate along with the plate holder 104 relative to the guide shaft 102. In at least some embodiments, the bone plate 30 is configured to angulate along with the plate holder 104 relative to the guide shaft 102. The bone-plate placement tool 20 defines a passageway 108 that extends through the bone-plate placement tool 20, such as through the guide shaft 102 and the plate holder 104. The passageway 108 can be configured to guide at least one of a drill bit and a bone anchor therethrough, through an aperture in the bone plate 30, and into the bone 70. The passageway 108 can pass through the guide shaft 102 and the plate holder 104.

Referring to FIGS. 4, 5, and 7, the guide shaft 102 has a guide shaft body 110, which has a shaft proximal end 110a and a shaft distal end 110b that are spaced from one another along a shaft longitudinal axis $A_S$ that extends along a first direction $D_1$. For instance, the shaft distal end 110b is spaced from the shaft proximal end 110a along a distal direction D. Conversely, the shaft proximal end 110a is spaced from the shaft distal end 110b along a proximal direction P, opposite the distal direction D. The guide shaft 102 can be elongate from the shaft proximal end 110a to the shaft distal end 110b along the shaft longitudinal axis $A_S$. The guide shaft body 110 can have an internal surface 112 (FIG. 5) that defines a bore 114 that extends through the guide shaft body 110 from the shaft proximal end 110a to the shaft distal end 110b along the shaft longitudinal axis $A_S$, where the bore 114 at least partially defines the passageway 108. The guide shaft 102 can be considered to be a guide sleeve in embodiments that implement the bore 114 and passageway 108.

The guide shaft body 110 has an outer surface 116 that extends from the shaft proximal end 110a to the shaft distal end 110b. The outer surface 116 can have at least a first outer-surface portion 107 that has a circular cross-sectional shape in a plane that is perpendicular to the shaft longitudinal axis $A_S$ or any other suitable cross-sectional shape such as a square, triangle, or other shape. The outer surface 116 is sized and configured to be supported by an aiming arm of the aiming guide 80 of FIG. 1. In one example, the first outer-surface portion 107 of the outer surface 116 has a first outer shaft dimension $d_{S1}$ in a plane that is perpendicular to the shaft longitudinal axis $A_S$, such as a diameter. In some embodiments as shown, the outer surface 116 can further have first and second engagement portions 109 and a third outer-surface portion 111. Each of the second outer-surface portion 109 and the third outer-surface portion 111 can be planar. Further, the second and third outer-surface portions 109 and 111 can be parallel to one another. The outer surface 116 can have a second outer shaft dimension $d_{S2}$ in a plane that is perpendicular to the shaft longitudinal axis $A_S$, the second outer shaft dimension $d_{S2}$ extending from the second outer-surface portion 109 to the third outer surface portion 111. As will be described further below, the second outer shaft dimension $d_{S2}$ can be sized such that the guide shaft body 110 can be received by the aiming guide 80, and the first outer shaft dimension $d_{S1}$ can be sized such that, when the guide shaft body 110 is rotated in the aiming guide 80, the guide shaft body 110 is retained in the aiming guide 80.

The guide shaft 102 and plate holder 104 are coupled to one another at a joint 118. The joint 118 can be a spherical joint. The joint 118 comprises a socket 122, and a head 120 received in the socket 122. For example, the guide shaft 102 can include the head 120 and the plate holder 104 can define the socket 122. The head 120 can extend from the shaft distal end 110b in the distal direction D. The head 120 can also extend from the shaft distal end 110b on opposite sides of the shaft longitudinal axis $A_S$, such as from all sides of the shaft longitudinal axis $A_S$. Thus, the longitudinal axis $A_S$ extends through the head 120. The head 120 can be attached to the shaft distal end 110b. For example, the head 120 can be integrally formed with the shaft distal end 110b. In alternative embodiments as described below, the head 120 can be removably attached to the shaft distal end 110b.

The head 120 has a wall 126 that includes an outer curved surface 128. The outer curved surface 128 can be at least partially spherical. For example, the outer curved surface 128 can be convex. Moreover, the outer curved surface 128 can have a first radius $R_1$. The wall 126 can further include an inner curved surface 130, opposite the outer curved surface 128. The inner curved surface 130 of the head 120 is at least partially spherical. For example, the inner curved surface 130 can be concave. Further, the inner curved surface 130 can conform to an outer curved surface portion 154 (FIG. 8) of the plate holder 104. The head 120 can also define a bore 124 that is in communication with the bore 114 of the guide shaft body 110 so as to at least partially define the passageway 108.

Referring more specifically to FIGS. 4, 5, 8, and 9, the plate holder 104 has an inner curved surface 132 that at least partially defines the socket 122. The inner curved surface 132 of the plate holder 104 and the outer curved surface 128 of the head 120 substantially conform to one another. The inner curved surface 132 is at least partially spherical. For example, the inner curved surface 132 can be concave. Moreover, the inner curved surface 132 of the plate holder 104 and outer curved surface 128 of the head 120 translate along one another when the head 120 is angulated in the socket 122. The inner curved surface 132 has a second radius $R_2$ that is substantially equal to, or just larger than, the first radius $R_1$.

The plate holder 104 has a holder proximal-end surface 104a and a holder distal-end surface 104b spaced from one another along a holder longitudinal axis $A_H$. The holder distal-end surface 104b faces the bone plate 30 when the bone plate 30 is fastened to the plate holder 104. The plate holder 104 further defines a proximal opening 134 that extends into the holder proximal-end surface 104a. The holder proximal opening 134 is sized and configured to receive the guide shaft 102 such that the guide shaft 102 extends out of the holder proximal opening 134 along the proximal direction P. The holder proximal opening 134 has a cross-sectional dimension $d_1$ in a plane perpendicular to the holder longitudinal axis $A_S$, the head 120 has a cross-sectional dimension $d_2$ in the plane, and the cross-sectional dimension $d_1$ of the holder proximal opening 134 is smaller than the cross-sectional dimension $d_2$ of the head 120 such that the head 120 is prevented from translating through the holder proximal opening 134 along the proximal direction P. For example, the cross-sectional dimension $d_1$ of the holder proximal opening 134 can be a diameter, and the cross-sectional dimension $d_2$ of the head 120 can be a segment length. The plate holder 104 can further define a bore 136 that extends through the plate holder 104 from the holder proximal end 104a to the holder distal end 104b along the holder longitudinal axis $A_H$. The bore 136 can be in communication with or open to the bore 114 of the guide shaft 102. Further, the bore 136 can at least partially define the passageway 108.

The plate holder 104 is configured to angulate relative to the guide shaft 102 along a range of angles such that the holder longitudinal axis $A_H$ can be aligned with the shaft longitudinal axis $A_S$ and can also be angularly offset with respect to the shaft longitudinal axis $A_S$ at a non-zero angle. Thus, the plate holder 104 can angulate in multiple planes, where each plane extends along the first direction $D_1$ and includes the shaft longitudinal axis $A_S$. In alternative embodiments, the plate holder 104 can be configured to angulate relative to the guide shaft 102 such that the plate holder 104 angulates in only a single plane that extends along the first direction $D_1$ and includes the shaft longitudinal axis $A_S$.

The plate holder 104 includes at least one plate. For example, the plate holder 104 can include a first plate 140 and a second plate 150. The first plate 140 has a proximal end 140a that defines the holder proximal end 104a. The proximal end 140a also defines the holder proximal opening 134. The first plate 140 further has a distal end 140b offset from the proximal end 140a along the holder longitudinal axis $A_H$. The distal end 140b defines the inner curved surface 132 that defines the socket 122.

The second plate 150 has a distal end 150b that defines the holder distal-end surface 104b that faces the bone plate 30 when the bone plate 30 is fastened to the plate holder 104. In some embodiments, the proximal end 140a and the distal end 150b can taper towards one another such that the plate holder 104 is tapered. For instance, the proximal end 140a can be spaced from the distal end 150b by a first distance on a first side of the plate holder 104 and by a second distance on a second side of the plate holder 104, opposite the first side, where the first distance is greater than the second distance. The tapered shape can ensure that the axes $A_S$ and $A_H$ intersect at the center point of radius $R_1$. This can permit the axis $A_S$ to be aligned with a bone-anchor aperture 216 (see FIG. 10) in the plate 30 for insertion of a bone anchor.

In at least some embodiments, the holder distal-end surface 104b can define at least one aperture configured to receive the at least one bone-plate fastener 106. The second plate 150 also has a proximal end 150a offset from the distal end 150b along the holder longitudinal axis $A_H$. The proximal end 150a has a proximal surface 152 defining a proximal curved portion 154. The proximal curved portion 154 is at least partially spherical. For example, the proximal curved portion 154 can be convex. The proximal curved portion 154 can have a curvature that conforms to the curvature of the inner curved surface 130 (FIG. 7) of the head 120. Thus, the proximal curved portion 154 can have a radius that is substantially equal to or just greater than the radius of the inner curved surface 130 of the head 120.

The second plate 150 defines a recess 156 that extends into the proximal end 150a of the second plate 150. The recess 150 is configured to receive the curved wall 126 of the head 120. The recess 150 extends into the proximal end 150a of the first plate 150 around the proximal curved portion 154. Thus, the recess 150 can be annular. The second plate is configured to fasten to the proximal end 140b of the first plate 140. The first and second plates 140 and 150 can fasten to one another via any suitable fastener, including but not limited to a weld. When the first and second plates 140 and 150 are fastened to one another, the socket 122 and the recess 156 align to define a channel configured to receive the curved wall 126 of the head 120. The curved wall 126 of the head 120 is translatable within the channel. Further, the curved wall 126 is captured in the channel between the first and second plates 140 and 150 so as to prevent translation of the head 120 along the proximal direction P and the distal direction D relative to the plate holder 104.

Referring more specifically to FIGS. 4 and 6, each of the at least one fastener 106 can be a projection 160 that extends from the plate holder 104. It will be understood that other types of fasteners can be employed. Each projection 160 is configured to engage a corresponding aperture 214 in the bone plate 30 so as to secure the plate holder 104 to the bone plate 30. The at least one fastener 106 can include a plurality of fasteners, each defining a projection 160. Each projection 160 extends from the plate holder 104 in the distal direction D. For example, each projection 160 can be a pin that extends from the plate holder 104 in the distal direction D. Each projection 160 includes a proximal end 160a and a distal end 160b spaced from the proximal end 160a along the distal direction D. Each projection 160 can be attached to the plate holder 104, such as removably attached to the plate holder 104. For example, the proximal end 160a can be sized and configured to be received in an aperture 158 defined in the holder distal end 104b of the plate holder 104. Alternatively, each projection 160 can be integrally formed with the plate holder 104.

The projections 160 can include one or more pins 161 that are solid from the proximal end 160a to the distal end 160b as shown in FIG. 4. For example, each of the pins 161 can have an outer perimeter that defines a closed shape around a central axis $A_P$ of the pin 161 as the pin 161 extends from the proximal end 160a to the distal end 160b.

Alternatively or additionally, the projections 160 can include one or more pins 163 that include one of a protrusion and a recess that engages a corresponding one of a recess and a protrusion defined by the bone plate 30 so as to secure the plate holder 104 to the bone plate 30. For example, each pin 163 can include a protrusion 166 having a shoulder or engagement surface 168 that abuts an opposing shoulder or engagement surface 220 of the bone plate 30 so as to secure the plate holder 104 to the bone plate 30.

The pin 163 can include a projection body 162 and at least one spring arm 164 attached to the projection body 162 and that is biased radially away from the central axis of the pin 163, so as to engage the bone plate 30 when the projection 160 is received in the aperture 214 in the bone plate 30. Each spring arm 164 can have a first end 164a attached to the projection body 162 and a second end 164b opposite the first end 164a, the second end 164b being free from attachment to the projection body 162. Further, each spring arm 164 can include the protrusion 166. Thus, each spring arm 164 can be configured to deflect inward as the protrusion rides along an internal surface of the aperture 214 in the bone plate 30 and spring radially outward to engage the protrusion 166 with the opposing shoulder or engagement surface 200 of the bone plate 30 when the protrusion 166 and engagement surface 200 are aligned. In at least some embodiments, the at least one spring arm 164 can include a pair of opposed spring arms 164. A slot 170 can extend into the distal end 160b, and opposed spring arms 164 can be defined on opposed sides of the slot 170. As shown in FIG. 4, at least some projections 160 can be devoid of spring arms and can fasten to the bone plate 30 by, for example, friction fit.

Turning now to FIG. 10, the bone plate 30 includes a bone-facing surface 202 and an outer surface 204 opposite the bone-facing surface 202. The bone plate 30 can have a first transverse side 206 and a second transverse side 208 opposite from one another. The first and second transverse sides 206 and 208 can extend from the bone-plate facing surface 202 to the outer surface 204. The bone plate 30 can additionally or alternatively have a first lateral side 210 and a second lateral side 212 opposite from one another. The first and second lateral sides 210 and 212 can extend from the bone-plate facing surface 202 to the outer surface 204. The first and second lateral sides 210 and 212 can extend from the first transverse side 206 to the second transverse side 208. It will be understood that embodiments of the disclosure are not limited to the specific bone plate shown in FIG. 10, and that alternative bone plates are contemplated.

The bone plate 30 defines a first bone-anchor aperture 216 configured to be aligned with the shaft longitudinal axis $A_S$ when the bone plate 30 is fastened to the bone-plate placement tool 20. Thus, the shaft longitudinal axis $A_S$ can extend through the first bone-anchor aperture 216 when the bone plate 30 is fastened to the bone-plate placement tool 20. Further, the bone-plate placement tool 20 is configured such that the shaft longitudinal axis $A_S$ aligns with the first bone-anchor aperture 216 over the full range of angles of the plate holder 104 relative to the guide shaft 102, without impeding with a path of a bone anchor or drill bit through the passageway 108. The first bone-anchor aperture 216 can extend through the bone plate 30 from the outer surface 204 to the bone-facing surface 202 so as to receive a bone anchor 40 (FIG. 1) to attach the bone plate 30 to the bone 70. The first bone-anchor aperture 216 can be threaded to receive a threaded head of a bone anchor. Further, the first bone-anchor aperture 216 can define variable-angle threading that permits a bone anchor to be inserted into the first bone-anchor aperture 216 at varying angles. Alternatively, the bone-anchor aperture 216 can be unthreaded.

The bone plate 30 defines at least one additional bone-anchor aperture 218, such as a plurality of additional bone-anchor apertures 218. The at least one additional bone-anchor aperture 218 is spaced from the first bone-anchor aperture 216 such that the at least one additional bone-anchor aperture 218 is offset from (i.e., not aligned with) the shaft longitudinal axis $A_S$ when the bone plate 30 is fastened to the bone-plate placement tool 20. The at least one additional bone-anchor aperture 218 extends through the bone plate 30 from the outer surface 204 to the bone-facing surface 202. At least one of the bone-anchor apertures 218 can be threaded to receive a threaded head of a bone anchor. Further, each bone-anchor aperture 218 can define variable-angle threading that permits a bone anchor to be inserted into the bone-anchor aperture 218 at varying angles. Alternatively, each additional bone-anchor aperture 218 can be unthreaded.

The bone plate 30 defines at least one, such as a plurality of, bone-plate fasteners 214 configured to engage a fastener 106 of the plate holder 104 so as to fasten the bone plate 30 to the plate holder 104. Each of the at least one bone-plate fastener 214 can define an aperture configured to receive a corresponding fastener 106 of the plate holder 104 so as to fasten the bone plate 30 to the plate holder 104. For example, each fastener 214 can be configured to receive a projection 160 that extends from the bone-plate placement tool 20. It will be understood that any other suitable fasteners can be used to releasably fasten the bone plate 30 to the plate holder 104.

Referring now to FIGS. 12-15, the alternative embodiment of the bone-plate placement tool 20 of FIG. 11 is shown. The bone-plate placement tool 20 comprises a guide shaft 402, a plate holder 404, and at least one bone-plate fastener 406. The plate holder 404 is coupled to the guide shaft 402 such that the plate holder 404 is configured to angulate relative to the guide shaft 402. In at least some embodiments, the plate holder 404 can angulate polyaxially relative to the guide shaft 402, although embodiments of the disclosure are not so limited. The at least one bone-plate fastener 406 is configured to releasably fasten the bone plate 30 to the plate holder 404 such that the bone plate 30 is positionally fixed relative to the plate holder 404 and is configured to angulate along with the plate holder 404 relative to the guide shaft 402. The bone-plate placement tool 20 defines a passageway 408 that extends through the bone-plate placement tool 20. The passageway 408 can be configured to guide at least one of a drill bit and a bone anchor therethrough and into an aperture in the bone plate 30. The passageway 408 can pass through the guide shaft 402 and the plate holder 404.

The guide shaft 402 has guide shaft body 410, which has a shaft proximal end 410a and a shaft distal end 410b that are spaced from one another along a shaft longitudinal axis $A_S$ that extends along a first direction $D_1$. For instance, the shaft distal end 410b is spaced from the shaft proximal end 410a along a distal direction D. Conversely, the shaft proximal end 410a is spaced from the shaft distal end 410b along a proximal direction P, opposite the distal direction D. The guide shaft 402 can be elongate from the shaft proximal end 410a to the shaft distal end 410b along the shaft longitudinal axis $A_S$. The guide shaft body 410 can have an internal surface 412 that defines a bore 414 that extends through the guide shaft body 410 from the shaft proximal end 410a to the shaft distal end 410b along the shaft longitudinal axis $A_S$, where the bore 414 at least partially defines the passageway 408. Thus, the guide shaft 402 can be considered to be a guide sleeve in embodiments that implement the bore 414 and passageway 408.

The guide shaft body 410 has an outer surface 416 that extends from the shaft proximal end 410a to the shaft distal end 410b. The outer surface 416 can have any suitable cross-sectional shape in a plane that is perpendicular to the shaft longitudinal axis $A_S$ such as a circle, square, triangle, or other shape. The outer surface 416 is sized and configured to be supported by an aiming arm of the aiming assembly 50. In one example, the outer surface 416 can be configured as shown and described in relation to FIG. 7 to include a first portion having a first outer dimension $d_{o1}$ and a second portion having a second outer dimension $d_{o2}$, where the first outer dimension $d_{o1}$ can be sized such that the guide shaft body 410 can be received by the aiming arm, and the second outer dimension $d_{o2}$ can be sized so as to retain the guide shaft body 410 in the aiming arm once it has been received.

The guide shaft 402 and plate holder 404 are coupled to one another at a joint 418. The joint 418 can be a spherical joint. The joint 418 comprises a socket 422, and a head 420 received in the socket 422. For example, the guide shaft 402 can include the head 420 and the plate holder 404 can define the socket 422. The head 420 can extend from the shaft distal end 410b in the distal direction D. The head 420 can also extend from the shaft distal end 410b on opposite sides of the shaft longitudinal axis $A_S$, such as from all sides of the shaft longitudinal axis $A_S$. Thus, the longitudinal axis $A_S$ extends through the head 420. The head 420 can be removably attached to the shaft distal end 410b. The head 420 has a wall 426 that includes an outer curved surface 428. The outer curved surface 428 can be at least partially spherical. For example, the outer curved surface 428 can be convex. Moreover, the outer curved surface 428 can have a first radius $R_1$. The head 420 can also define a bore 424 that is in communication with the bore 414 of the guide shaft body 410 so as to at least partially define the passageway 408.

Referring to FIGS. 15 and 16, the head 420 is removably attached to the guide shaft body 410. The head 420 can have any suitable fastener attached thereto that is configured to removably fasten the head 420 to the guide shaft body 410. For example, the guide shaft 402 can comprise a bearing stud 430 that includes the head 420 and a fastener configured to removably fasten the head to the guide shaft body 410. The fastener can include a shank 438 that extends from the head 420 along the proximal direction P to a proximal end 438a of the shank 438. The shank 438 can have an outer surface 440 that is sized to be received into the shaft bore 414 of the guide shaft body 410 through the shaft distal end 410b. The shank 438 can include an internal surface 442 that defines a shank bore 444 that is in communication with the shaft bore 414 of the guide shaft body 410 when the shank 438 is received in the guide shaft body 410, the shank bore 444 of the shank 438 at least partially defining the passageway 408.

The bearing stud 430 can define at least one of a protrusion and a recess that engages a corresponding one of a recess and a protrusion defined by the guide shaft body 410 so as to secure the bearing stud 430 to the guide shaft body 410. For example, the shank 438 can include at least one protrusion 446 that extends radially from the shank 438 so as to engage a corresponding recess 448 that extends radially into the guide shaft body 410.

Further, the shank 438 can include a shank body 450 and at least one spring arm 452 that is attached to the shank body 450 and that is biased in a radial direction, perpendicular to both the proximal direction P and distal direction D, so as to engage the guide shaft body 410. Each spring arm 452 can have a first end 452a attached to the shank body 450 and a second end 452b, opposite the first end 452a, the second end 452b being free from attachment to the shank body 450. In one example, at least one slot 454 can extend into the shank proximal end 438a and through the shank 438 in the radial direction. The shank 438 can define a pair of opposed spring arms 452 on opposed sides of the slot 454. It will be understood that each spring arm 452 can be implemented in any suitable alternative manner. For example, each spring arm 452 can be defined by a "U"-shaped cutout in the shank body 450 such that the spring arm 452 is disposed within the shank body 450 between the shank proximal end 438a and the shank distal end 438b.

Each of the at least one spring arm 452 can include the protrusion 446. Further, each spring arm 452 can be biased in a radial direction, perpendicular to the proximal direction P and distal direction D, so as to engage the protrusion 446 with the recess 448 of the guide shaft body 410. Each spring arm 452 can be configured to deflect inward as the protrusion 446 rides along the internal surface 412 of the guide shaft 410 and spring radially outward to engage the protrusion 446 of the shank 438 with the recess 448 of the guide shaft body 410 when the protrusion 446 and recess 448 are aligned. In alternative embodiments, the shank 438 can define at least one recess (not shown) that extends in the radial direction into the shank 438 so as to engage a corresponding protrusion (not shown) that extends in the radial direction from the guide shaft body 410. Further, in alternative embodiments, the outer surface 416 of the guide shaft body 410 can be sized and configured to be received in the shank bore 454, rather than the shank 438 being received in the shaft bore 414.

Referring more specifically to FIGS. 12 to 15, the plate holder 404 has an inner curved surface 432 that at least partially defines the socket 422. The inner curved surface 432 of the plate holder 404 and the outer curved surface 428 of the head 420 substantially conform to one another. The inner curved surface 432 is at least partially spherical. For example, the inner curved surface 432 can be concave. Moreover, the inner curved surface 432 of the plate holder 404 and outer curved surface 428 of the head 420 translate along one another when the head 420 is angulated in the socket 422. The inner curved surface 432 has a second radius $R_2$ that is substantially equal to or just greater than the first radius $R_1$.

The plate holder 404 has a holder proximal-end surface 404a and a holder distal-end surface 404b spaced from one another along a holder longitudinal axis $A_H$. The holder distal-end surface 404b faces the bone plate 30 when the bone plate 30 is fastened to the plate holder 404. In some embodiments, the bone-plate placement tool 20 can be configured such that the axes $A_S$ and $A_H$ intersect at the center point of the sphere that defines radius $R_1$. This can permit the axis $A_S$ to be aligned with a bone-anchor aperture 516 (see FIG. 17) in the plate 30 for insertion of a bone anchor.

The plate holder 404 further defines a proximal opening 434 that extends into the holder proximal-end surface 404a. The holder proximal opening 434 is sized and configured to receive the guide shaft 402 such that the guide shaft 402 extends out of the holder proximal opening 434 along the proximal direction P. The holder proximal opening 434 has a cross-sectional dimension $d_1$ in a plane perpendicular to the holder longitudinal axis $A_S$, the head 420 has a cross-sectional dimension $d_2$ in the plane, and the cross-sectional dimension $d_1$ of the holder proximal opening 434 is smaller than the cross-sectional dimension $d_2$ of the head 420 such that the head 420 is prevented from translating through the holder proximal opening 434 along the proximal direction P. For example, the cross-sectional dimension $d_1$ of the holder proximal opening 434 can be a diameter, and the cross-sectional dimension $d_2$ of the head 420 can be a segment length. The plate holder 404 can further define a bore 436 that extends through the plate holder 404 from the holder proximal end 404a to the holder distal end 404b along the holder longitudinal axis $A_H$. The bore 436 can be in communication with or open to the opening 434. Further, the bore 436 can be in communication with or open to the bore 414 of the guide shaft 402. The bore 436 can at least partially define the passageway 408.

The plate holder 404 is configured to angulate relative to the guide shaft 402 along a range of angles such that the holder longitudinal axis $A_H$ can be aligned with the shaft longitudinal axis $A_S$ and can also be angularly offset with respect to the shaft longitudinal axis $A_S$ at a non-zero angle. Thus, the plate holder 404 can angulate in multiple planes, where each plane extends along the first direction $D_1$ and includes the shaft longitudinal axis $A_S$. In alternative embodiments, the plate holder 404 can be configured to angulate relative to the guide shaft 402 such that the plate holder 404 angulates in only a single plane that extends along the first direction $D_1$ and includes the shaft longitudinal axis $A_S$.

The plate holder 404 can include at least one plate. For example, the plate holder 404 can include a first plate 440 that has a proximal end surface 440a that at least partially defines the holder proximal end 404a. The proximal end surface 440a also defines the holder proximal opening 434. The first plate 440 further has a distal end surface 440b that is opposite the proximal end surface 440a along the holder longitudinal axis $A_H$.

The distal end surface 440b includes a curved portion 432 that defines the socket 422. Further, at least a portion of the distal end surface 440b faces the bone plate 30 when the bone plate 30 is fastened to the plate holder 404. The first plate 440 has a first transverse side 440c and a second transverse side 440d offset from one another along a second direction $D_2$, perpendicular to the first direction $D_1$. The first plate 440 has a first lateral side 440e and a second lateral side 440f offset from one another along a third direction, perpendicular to both the first and second directions $D_1$ and $D_2$.

The plate holder 404 can include at least one wall 456, where each wall 456 extends in the distal direction D from a different one of the first transverse side 440c, the second transverse side 440d, the first lateral side 440e, and the second lateral side 440f. For example, the plate holder 404 can include a first transverse wall 456a that extends from the first transverse side 440c in the distal direction D. The plate holder can include first and second lateral walls 456b and 456c that extend from the first and second lateral sides 440e and 440f along the distal direction D. Each of the at least one wall 456 can include an inner surface and an outer surface opposite the inner surface. The inner surfaces can be configured to abut the bone plate 30 when the bone plate 30 is fastened to the plate holder 404. Further, the inner surfaces of the at least one wall 456 can define a recess 457 that extends into the distal end 404b to the distal end surface 440b and that is configured to at least partially receive the bone plate 30. For example, the plurality of walls 456 can conform to an outer perimeter of the bone plate 30. In alternative embodiments, the plate holder 404 can be devoid of walls 456, or the plate holder 404 can includes walls that are configured in a manner different than that shown.

Each of the at least one fastener 406 can include a projection that extends from the plate holder 404. Each projection can be integrally formed with the plate holder 404. Alternatively, each projection can be attached to the plate holder 404, such as removably attached to the plate holder 404. It will be understood that other types of fasteners can be employed. Each projection can be configured to engage a corresponding aperture or recess 514 in the bone plate 30 so as to secure the plate holder 404 to the bone plate 30. The at least one fastener 406 can include a plurality of fasteners, each defining a projection.

For example, the at least one fastener 406 can include at least one projection 460 (labeled in FIG. 15), such as a pair of projections 460, that extends inward from the first transverse side 440c towards the second transverse side 440d and into the recess 457. The at least one projection 460 can extend into a recess 515 in a first transverse side 506 of the bone plate 30 so as to secure the first transverse side 440c of the plate holder 404 to the first transverse side 506 of the bone plate 30.

Additionally or alternatively, the at least one fastener 406 can include at least one projection 464 that defines a spring arm that extends from the plate holder 404, such as a pair of spring arms. Each spring arm 464 can extend from the second transverse side 440d in the distal direction D. Each spring arm 464 can have a first end 464a that is attached to the plate holder 404 and a second end 464b offset from the first end 464a, the second end 464b being free from attachment to the plate holder 404. Each spring arm 464 can include a protrusion 466 that extends from the spring arm 464 in the second direction $D_2$. Each protrusion 466 can include a shoulder or engagement surface 468 that abuts an opposing shoulder or engagement surface 522 of the bone plate 30 so as to secure the plate holder 404 to the bone plate 30.

Each spring arm 464 can be biased in the second direction $D_2$ so as to engage the protrusion 466 with the recess in the corresponding opening 514 of the bone plate 30. Further, each spring arm 464 can be configured to deflect in a direction towards the first transverse side 440c as the protrusion 466 rides along the internal surface of the opening 514 in the bone plate 30 and spring back away from the first transverse side 440c to engage the protrusion 466 with the recess in the opening 514 of the bone plate 30 when the protrusion 466 and recess are aligned. In an alternative embodiment, one or more of the spring arms 464 can be configured to deflect in a direction away from the first transverse side 440c as the protrusion 466 rides along the internal surface of the opening 514 in the bone plate 30 and spring back towards the first transverse side 440c to engage the protrusion 466 with the recess in the opening 514 of the bone plate 30 when the protrusion 466 and recess are aligned.

Each spring arm 464 can have first and second broadsides 464c and 464d (labeled in FIG. 15) that oppose one another, and first and second edges 464e and 464f (labeled in FIG. 12) that oppose one another. The first and second edges 464e and 464f can extend from the first broadside 464c to the second broadside 464d. Each spring arm 464 can include the protrusion 466, which can extend away from one of the first and second broadsides 464c and 464d in the second direction $D_2$. Each of the first and second broadsides 464c and 464d can define a width from the first edge 464e to the second edge 464f that is greater than a thickness of the first and second edges 464e and 464f from the first broadside 464c to the second broadside 464d.

Turning now to FIGS. 15 and 17, the bone plate 30 includes a bone-facing surface 502 and an outer surface 504 opposite the bone-facing surface 502. The bone plate 30 can have a first transverse side 506 and a second transverse side 508 opposite from one another. The first and second transverse sides 506 and 508 can extend from the bone-plate facing surface 502 to the outer surface 504. The bone plate 30 can additionally or alternatively have a first lateral side 510 and a second lateral side 512 opposite from one another.

The first and second lateral sides 510 and 512 can extend from the bone-plate facing surface 502 to the outer surface 504. The first and second lateral sides 510 and 512 can extend from the first transverse side 506 to the second transverse side 508.

The bone plate 30 defines a first bone-anchor aperture 516 configured to be aligned with the shaft longitudinal axis $A_S$ when the bone plate 30 is fastened to the bone-plate placement tool 20. Thus, the shaft longitudinal axis $A_S$ can extend through the first bone-anchor aperture 516 when the bone plate 30 is fastened to the bone-plate placement tool 20. Further, the bone-plate placement tool 20 is configured such that the shaft longitudinal axis $A_S$ aligns with the first bone-anchor aperture 216 over the full range of angles of the plate holder 104 relative to the guide shaft 102, without impeding with a path of a bone anchor or drill bit through the passageway 408. The first bone-anchor aperture 516 can extend through the bone plate 30 from the outer surface 504 to the bone-facing surface 502 so as to receive a bone anchor 40 (FIG. 11) to attach the bone plate 30 to the bone 70. The first bone-anchor aperture 516 can be threaded to receive a threaded head of a bone anchor. Further, the first bone-anchor aperture 516 can define variable-angle threading that permits a bone anchor to be inserted into the first bone-anchor aperture 516 at varying angles. Alternatively, the bone-anchor aperture 516 can be unthreaded.

The bone plate 30 defines at least one additional bone-anchor aperture 518, such as a plurality of additional bone-anchor apertures 518. The at least one additional bone-anchor aperture 518 is spaced from the first bone-anchor aperture 516 such that the at least one additional bone-anchor aperture 518 is offset from (i.e., not aligned with) the shaft longitudinal axis $A_S$ when the bone plate 30 is fastened to the bone-plate placement tool 20. The at least one additional bone-anchor aperture 518 extends through the bone plate 30 from the outer surface 504 to the bone-facing surface 502. At least one of the bone-anchor 518 can be threaded to receive a threaded head of a bone anchor. The at least one additional bone-anchor aperture 518 extends through the bone plate 30 from the outer surface 204 to the bone-facing surface 202. At least one of the bone-anchor apertures 518 can be threaded to receive a threaded head of a bone anchor. Further, each bone-anchor aperture 518 can define variable-angle threading that permits a bone anchor to be inserted into the bone-anchor aperture 518 at varying angles. Alternatively, each additional bone-anchor aperture 518 can be unthreaded.

The bone plate 30 defines at least one, such as a plurality of, bone-plate fasteners 514 configured to engage a fastener 406 of the plate holder 404 so as to fasten the bone plate 30 to the plate holder 404. Each bone-plate fastener 514 can define an aperture or recess configured to receive a corresponding fastener 406 of the plate holder 404 so as to fasten the bone plate 30 to the plate holder 404. For example, each fastener 514 can be configured to receive a projection 460 that extends from the bone-plate placement tool 20. It will be understood that any other suitable fasteners can be used to releasably fasten the bone plate 30 to the plate holder 404.

The at least one bone-plate fastener 514 can include at least one recess 515, such as a pair of recesses 515, each configured to receive a projection 460 that extends from the plate holder 404. The at least one recess 515 can extend into the first transverse side 506 of the bone plate 30. The at least one fastener 514 can additionally or alternatively include at least one aperture 520, such as a pair of apertures 520, each configured to receive a projection 464 such as a spring arm that extends from the plate holder 404. The at least one aperture 520 can extend into the outer surface 504 of the bone plate 30 towards the bone-facing surface 502. Further, each aperture 520 can define a shoulder or engagement surface 522 that abuts a shoulder or engagement surface 468 of a corresponding projection 464 of the plate holder 404 so as to secure the plate holder 404 to the bone plate 30.

Turning back to FIGS. 1 and 11, each system 10 can include an aiming assembly 50 configured to support the bone-plate placement tool 20 at a location that is spaced from the intramedullary nail along a first direction $D_1$ such that an axis $A_S$ of the bone-plate placement tool 20 is aligned with a bone-anchor opening in the intramedullary nail 60. The aiming assembly 50 can include an aiming guide 80 configured to support the bone-plate placement tool 20, and a connecting arm 90 configured to removably attach the aiming guide 80 to the intramedullary nail 60. It will be understood that in alternative embodiments, the aiming guide 80 and connecting arm 90 can be integral to one another or permanently attached to one another.

Figure 18:
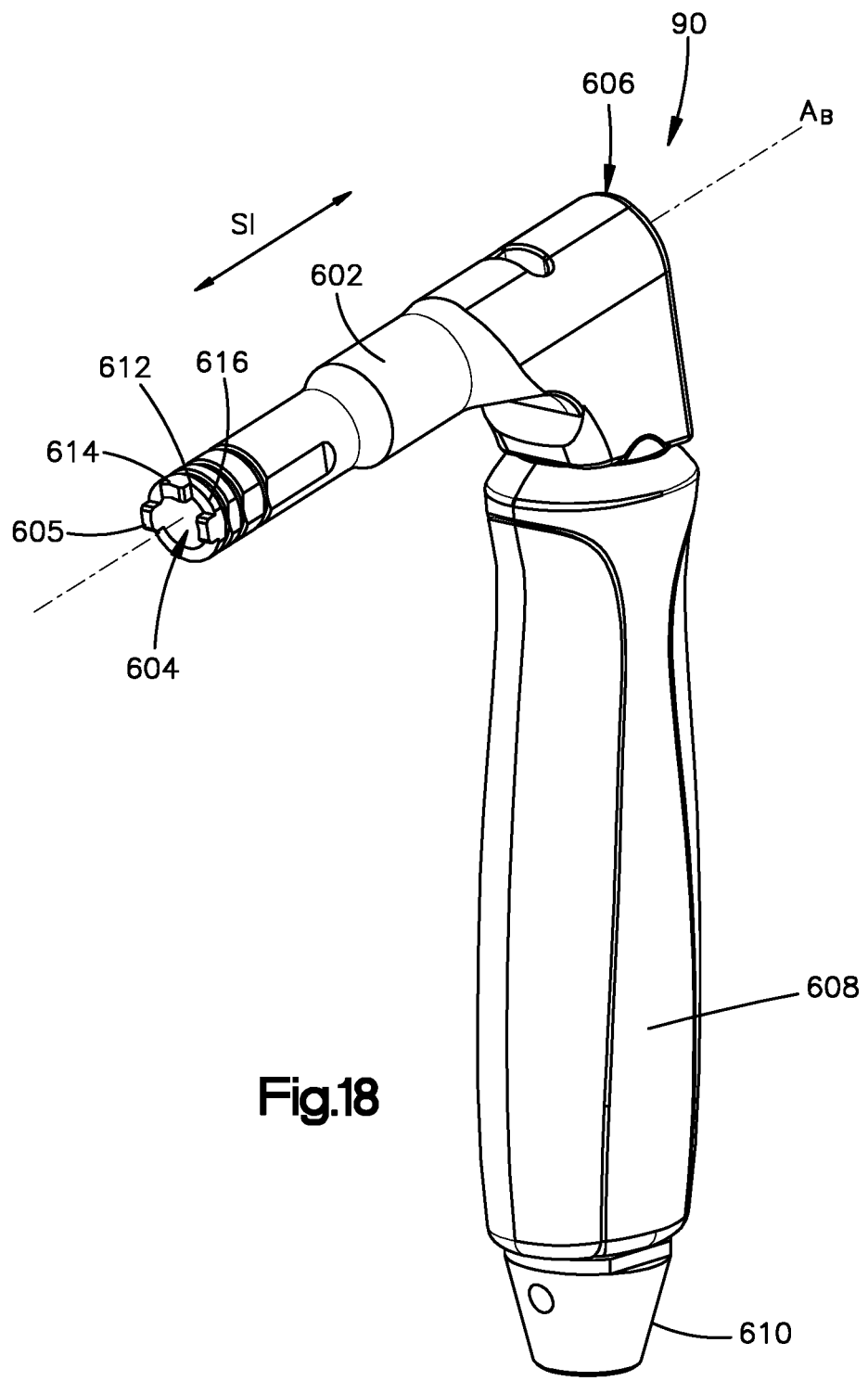
FIG. 18 shows a perspective front view of a handle of the aiming assemblies of FIGS. 1 and 11 according to one embodiment.

Referring more specifically to FIG. 18, the connecting arm 90 can define a handle configured to be held by an operator as the operator guides and forces the intramedullary nail 60 into the medullary canal of the bone 70. The handle 90 can have a handle body 602 that includes a handle leading end 604, and a handle trailing end 606 that is spaced from the handle leading end 604 along a handle body longitudinal axis $A_B$ that extends along the superior-inferior direction SI.

The handle 90 can include a handgrip 608 that extends from the handle body 602 at an angle with respect to the handle body longitudinal axis $A_B$. The angle can be a non-zero angle. For example, the angle can be substantially perpendicular to the handle body longitudinal axis $A_B$. The handgrip 608 can extend from the handle body 602 at the handle trailing end 606 such that the handle has a generally "L" shape. Note that, in alternative embodiments, the handgrip 608 can be configured differently than that shown. For example, the handgrip 608 can extend from locations other than the handle trailing end 606, such as along a middle of the handle body 602 to form a "T" shape. The handgrip 608 can include a fastener 610 configured to fasten to a fastener 712 of the aiming guide 80. The fastener 610 can be any suitable fastener such as a recess configured to receive a threaded rod 718 of the aiming guide 80.

The handle leading end 604 can be configured to interlock with the intramedullary nail 60 so as to prevent rotation of the handle 90 about the handle longitudinal axis $A_S$ relative to the intramedullary nail 60. The handle leading end 604 can include a fastener 612 that fastens to a proximal end of the intramedullary nail 60. In one embodiment, the fastener 612 can comprise at least one of a protrusion and a recess that is configured to engage a corresponding one of a recess and a protrusion of the intramedullary nail 60. For example, the fastener 612 can comprise at least one protrusion 614, such a plurality of protrusions or teeth. Each protrusion 614 can be configured to engage at least one corresponding recess in the intramedullary nail 60. Each of the at least one protrusion 614 can extend from a leading end surface 605 of the handle leading end 604 towards the handle trailing end 606. The fastener 604 can define at least one recess 616, such as a plurality of recesses, that extends into the handle leading end surface 605 towards the handle trailing end 606 to a floor of the recess 616. Each of the at least one recess 616 can be configured to receive a corresponding protrusion of the intramedullary nail 60. Further, in embodiments having a plurality of protrusions 614, each of the at least one recess 616 can extend between a pair of the protrusions 614. In such embodiments, the protrusions 614 and recesses 616 can alternate as they extend around the handle leading end 604.

Figure 19:
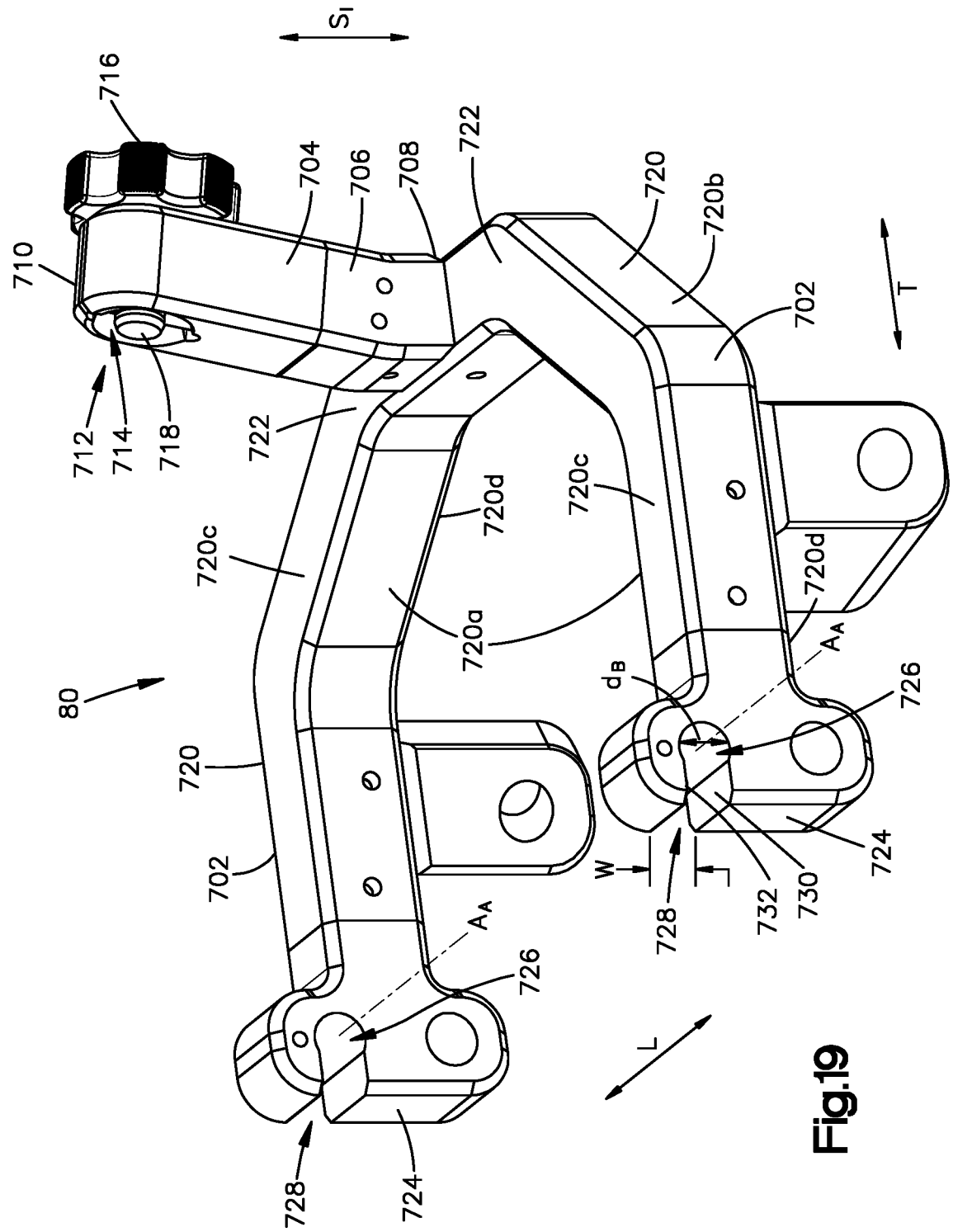
FIG. 19 shows a perspective side view of an aiming guide of the aiming assemblies of FIGS. 1 and 11 according to one embodiment.

Turning now to FIG. 19, the aiming guide 80 can include at least one aiming arm 702 configured to support the bone-plate placement tool 20, and an extension 704 configured to connect the aiming arm 702 to the handle 90. In some embodiments, the aiming guide 80 can include a pair of aiming arms 702. The extension 704 extends generally along the superior-inferior direction SI. The extension 704 includes an extension arm body 706 having a first extension end 708 and a second extension end 710 spaced from one another generally along the superior-inferior direction SI. The first extension end 708 is attached to the at least one aiming arm 702. The second extension end 710 includes at least one fastener 712 configured to removably fasten the aiming guide 80 to the handle 90. In one example, the fastener 712 includes a recess 714 that is defined in the extension arm body 706 and configured to receive the fastener 610 (FIG. 18) of the handgrip 608 of the handle 90. Alternatively or additionally, the fastener 714 can include a knob 716 coupled to an externally threaded shaft 718 that can engage a corresponding internally threaded recess in the handgrip 608 of the handle 90. It will be understood that the fastener 712 can be any suitable alternative fastener.

The aiming arm 702 has an aiming arm body 720 having a first aiming arm end 722 and a second aiming arm end 724 spaced from one another. The first aiming arm end 722 is coupled to the first extension end 708 of the extension 704. The aiming arm body 720 extends away from the first extension end 708 to the second aiming arm end 724 along a lateral direction L that is perpendicular to the superior-inferior direction SI, and along a transverse direction T that is perpendicular to both the lateral direction L and the superior-inferior direction SI. The aiming arm body 720 has an inner surface 720a and an outer surface 720b that oppose one another. The inner surface 720a is configured to face towards the bone 70 (see e.g., FIGS. 1 and 11) when the aiming guide 80 is coupled to an intramedullary nail such as nail 60 in FIGS. 1 and 11. Thus, the aiming arm 720 is configured such that, when the aiming guide 80 is coupled to the intramedullary nail, the aiming arm 702 extends around the bone 70 and is spaced from the bone 70 such that the aiming arm 702 is disposed outside of the patient's body.

The aiming arm body 720 can further include a first side surface 720c and a second side surface 720d that oppose one another. The first and second side surfaces 720c and 720d can extend between the inner and outer surfaces 720a and 720b. The aiming arm body 720 can define an aiming bore 726 that extends through the inner and outer surfaces 720a and 720b along an aiming bore axis $A_4$. The aiming bore 726 is configured to receive the guide shaft (e.g., 102 in FIG. 2-5 or 402 in FIGS. 12-15) of the bone-plate placement tool 20. The aiming bore 726 can have any suitable cross-sectional shape in a plane that is perpendicular to the aiming bore axis $A_4$. For example, the aiming bore 726 can have a cross-sectional shape that conforms to the cross-sectional shape of the first portion (e.g., 107 in FIG. 7) of the guide shaft. Thus, the aiming bore 726 can have an aiming bore cross-sectional dimension $d_B$, such as a diameter, along a direction that is perpendicular to the aiming bore axis $A_4$, where the aiming bore cross-sectional dimension $d_B$ is greater than the first outer shaft dimension $D_{S1}$ (see FIG. 7).

The aiming arm body 720 can further define an aiming arm slot 728 configured to receive the guide shaft (e.g., 102 in FIG. 2-5 or 402 in FIGS. 12-15) of the bone-plate placement tool 20 into the aiming bore 726. The aiming arm slot 728 can extend through the inner and outer surfaces

720a and 720b. Further, the aiming arm slot 728 can extend into an outer surface of the aiming arm body 720 and to the aiming bore 726. For example, the aiming arm slot 728 can extend into the aiming arm end 724 to the aiming bore 726. It will be understood that the aiming arm slot 728 can extend into any other suitable surface of the aiming arm body 720 such as (without limitation) the first side surface 720c or the second side surface 720c. The aiming arm slot 728 is defined between first and second internal surfaces 730 and 732 of the aiming arm body 720 that oppose one another. The first and second internal surfaces 730 and 732 can be planar. Further, the first and second internal surfaces 730 and 732 can be parallel to one another. The first and second internal surfaces 730 and 732 are spaced from one another by a slot cross-sectional dimension $d_{SL}$. The slot cross-sectional dimension $d_{SL}$ is smaller than the aiming bore cross-sectional dimension $d_B$. Further, the slot cross-sectional dimension $d_{SL}$ is smaller than the first outer shaft dimension $d_{S1}$ and greater than the second outer shaft dimension $d_{S2}$.

Figure 21:
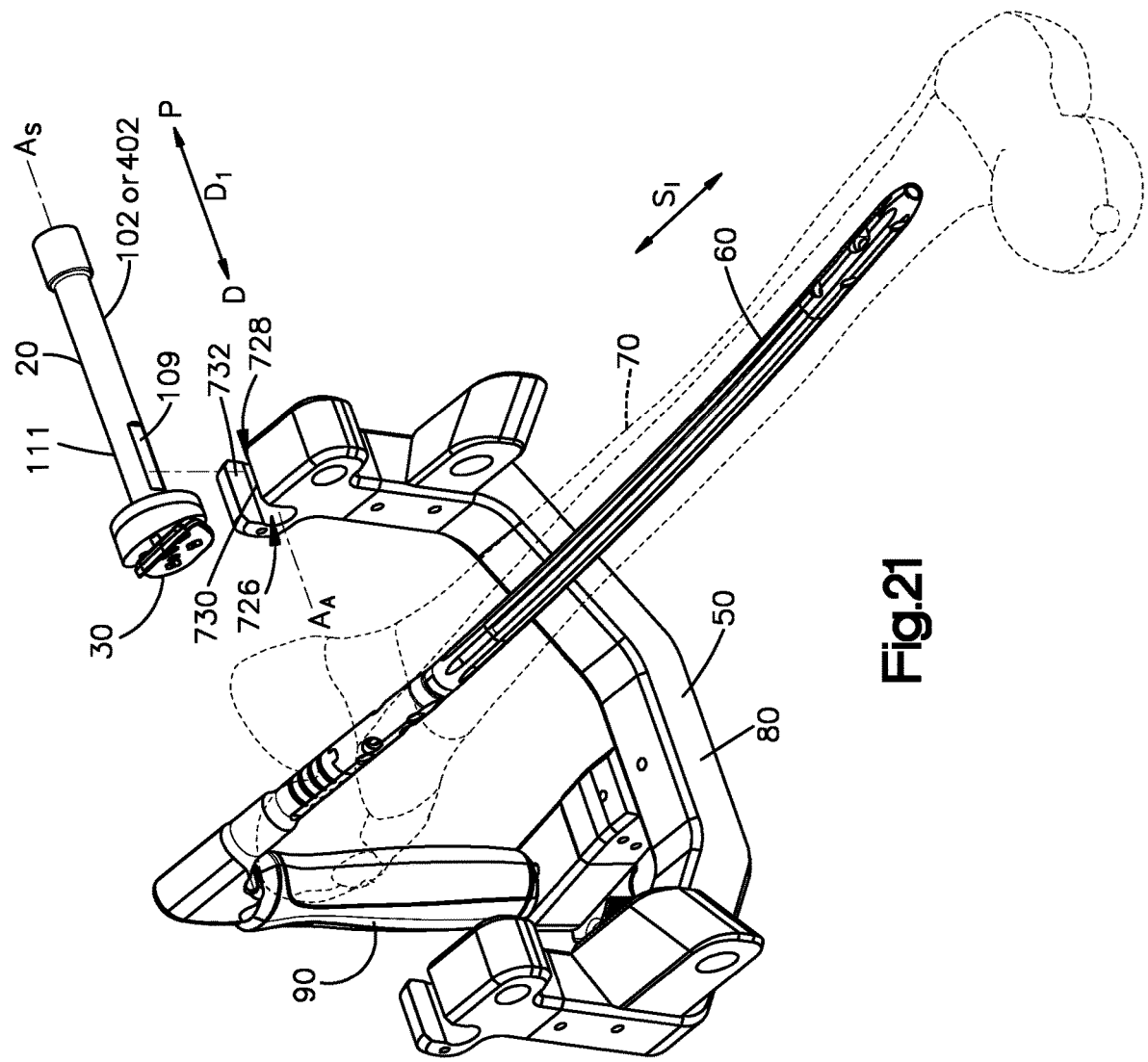
FIG. 21 shows a perspective view of a system comprising the intramedullary nail and handle as shown in FIG. 20 with an aiming guide attached to the handle, the aiming guide receiving a variable-angle bone-plate placement tool that is fastened to a bone plate.

In operation, and with reference to FIGS. 19 and 21, the second and third outer surface portions (e.g., 109 and 111) of the guide shaft (e.g., 102 or 402) can be aligned with the first and second internal surfaces 730 and 732 along a direction that extends from the aiming arm slot 728 to the aiming bore 726 and along the first direction $D_1$. The guide shaft (e.g., 102 or 402) can then be translated through the aiming arm slot 728 and into the aiming arm bore 728. As the guide shaft (e.g., 102 or 402) is translated through the aiming arm slot 728, the second and third outer surface portions (e.g., 109 and 111) of the guide shaft (e.g., 102 or 402) face the first and second internal surfaces 730 and 732 of the aiming arm body 720, respectively. Once the guide shaft (e.g., 102 or 402) is received in the aiming arm bore 728, the guide shaft can be rotated about the shaft longitudinal axis $A_S$ such that the second and third outer surface portions (e.g., 109 and 111) of the guide shaft (e.g., 102 or 402) are no longer aligned with the first and second internal surfaces 730 and 732 along the direction that extends from the aiming arm slot 728 to the aiming bore 726. Further, the guide shaft can be translated within the aiming bore 726 along the first direction $D_1$ so that the second and third outer surface portions (e.g., 109 and 111) of the guide shaft (e.g., 102 or 402) are no longer aligned with the first and second internal surfaces 730 and 732 along the first direction $D_1$. Since the first outer shaft dimension $d_{S1}$ is greater than the slot cross-sectional dimension $d_{SL}$, the guide shaft (e.g., 102 or 402) is captured in the aiming bore 726 and prevented from translating out of the aiming arm slot 728.

Figure 20:
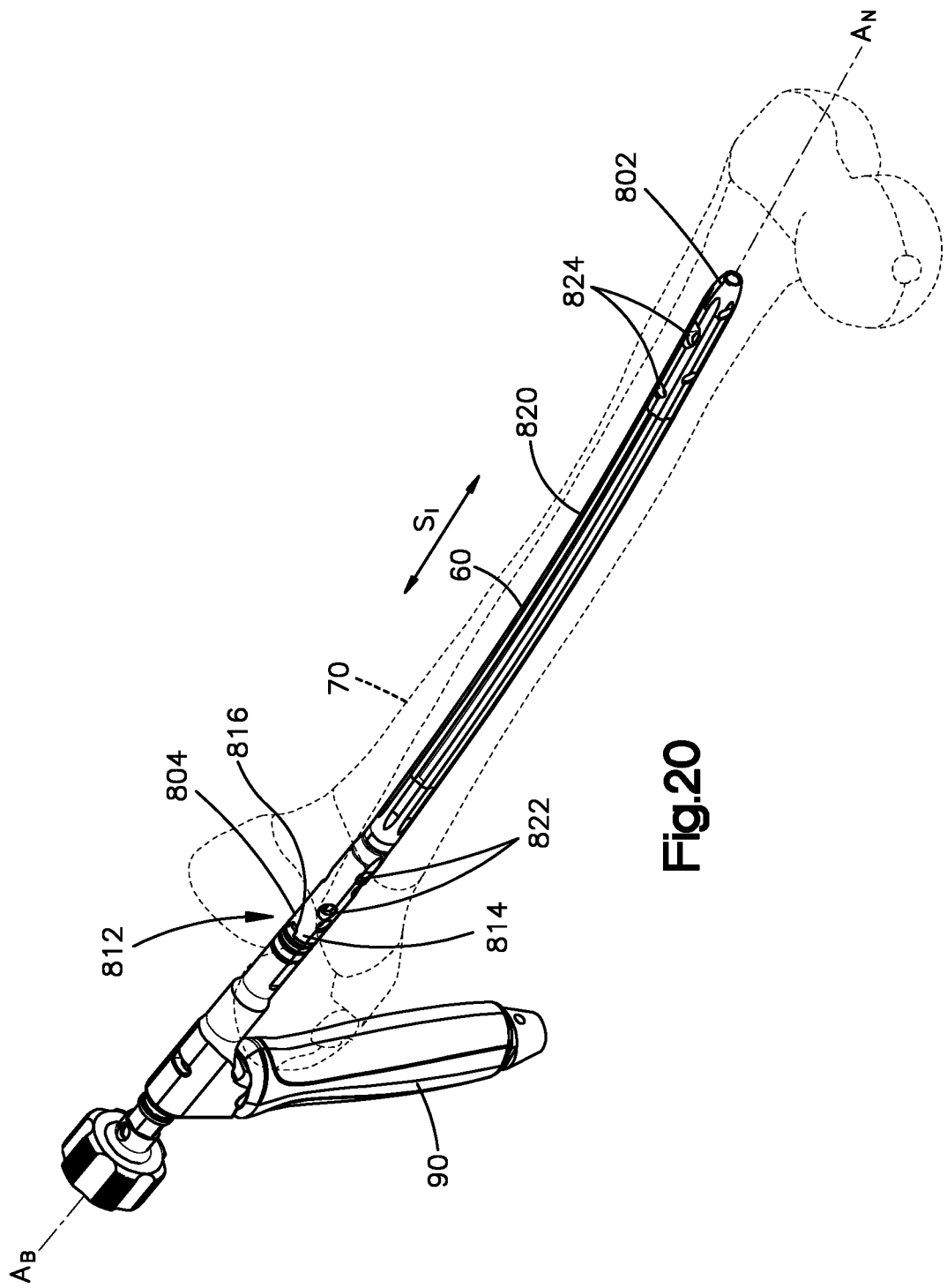
FIG. 20 shows a perspective view of an intramedullary nail that is received in medullary canal of a bone, the intramedullary nail coupled to the handle of FIG. 18.

Referring to FIG. 20, an intramedullary nail 60 is shown according to one embodiment. It will be understood that intramedullary nail 60 is but one example, and that other intramedullary nails can be used with the system described herein. The intramedullary nail 60 has a nail leading or insertion end 802, and a nail trailing end 804 one another along the superior-inferior direction SI. The nail leading and trailing ends 802 and 804 can be spaced from one another along a central nail axis $A_N$ that can be straight or bent. Further, the intramedullary nail 60 has an outer surface 820 that extends between the nail leading and trailing ends 802 and 804, such as from the nail leading end 802 to the nail trailing end 804.

The nail trailing end 804 can include a fastener 812 that is configured to engage the fastener 612 of the handle 90 so as to rotatably fix the handle 90 and intramedullary nail 60 relative to one another with respect to rotation about the handle body longitudinal axis $A_B$. In one embodiment, the fastener 812 can comprise at least one of a protrusion and a recess that is configured to engage a corresponding one of a recess and a protrusion of the handle 90. For example, the fastener 812 can comprise at least one protrusion 814, such a plurality of protrusions or teeth. Each protrusion 814 can be configured to engage at least one corresponding recess 616 in the handle 90. Each of the at least one protrusion 814 can extend from a nail trailing end surface of the intramedullary nail 60 towards the nail leading end 802. The fastener 812 can define at least one recess 816, such as a plurality of recesses, that extends into the nail trailing end surface towards the nail leading end 802 to a floor of the recess 816. Each of the at least one recess 816 can be configured to receive a corresponding protrusion 614 of the handle 90. Further, in embodiments having a plurality of protrusions 814, each of the at least one recess 816 can extend between a pair of the protrusions 814. Thus, in such embodiments, the protrusions 814 and recesses 816 can alternate around the nail trailing end 804.

The intramedullary nail 60 further defines a set of one or more trailing end apertures 822 that extend through the outer surface 820 at the nail trailing end 804, and a set of one or more leading end apertures 824 that extend through the outer surface 820 at the nail leading end 802. The set of one or more trailing end apertures 822 are positioned to be disposed on a first side of a fracture in the bone 70, and the set of one or more leading end apertures 824 are positioned to be disposed on a second side of the fracture in the bone 70. Each leading end aperture 822 and each trailing end aperture 824 is configured to receive a bone anchor such that the bone anchor fixedly attaches the intramedullary nail 60 to the bone 70.

Now with reference to FIGS. 20-24, an example embodiment of a method of implanting an intramedullary nail 60 will be described. As shown in FIG. 20, the handle 90 is coupled to the intramedullary nail 60, and the intramedullary nail 60 is driven into the medullary canal of the bone 70 by the handle 90. In FIG. 21, the aiming guide 80 of the aiming assembly 50 is fastened to the handle 90. Further, in FIGS. 21 and 22, the bone plate 30 is fastened to the plate holder (e.g., 104 in FIG. 2-5 or 404 in FIGS. 12-15) of the bone-plate placement tool 20 such that the bone plate 30 is configured to angulate with the plate holder (e.g., 104 or 404) relative to a guide shaft (e.g., 102 in FIG. 2-5 or 402 in FIGS. 12-15) of the bone-plate placement tool 20.

The bone-plate placement tool 20 is coupled to the aiming assembly 50 such that the shaft longitudinal axis $A_S$ of the bore (e.g., 114 in FIG. 5 or 414 in FIG. 15) that extends through the guide shaft (e.g., 102 or 402) is aligned with both the bone-anchor aperture 215 or 516 in the bone plate 30 and a bone-anchor aperture that extends into an outer surface of the intramedullary nail 60. The bone-placement tool 20 can be coupled to the aiming assembly 50 as described above in relation to the aiming bore 726, although it will be understood that the bone-placement tool 20 can be coupled to the aiming assembly 50 in another suitable manner. The bone-plate placement tool 20 and bone plate 30 are advanced along the first direction $D_1$ towards an outer surface of the bone 70 until the bone plate 30 contacts the outer surface of the bone 70 causing the bone plate 30 to angulate into alignment against the outer surface of the bone 70.

Figure 22:
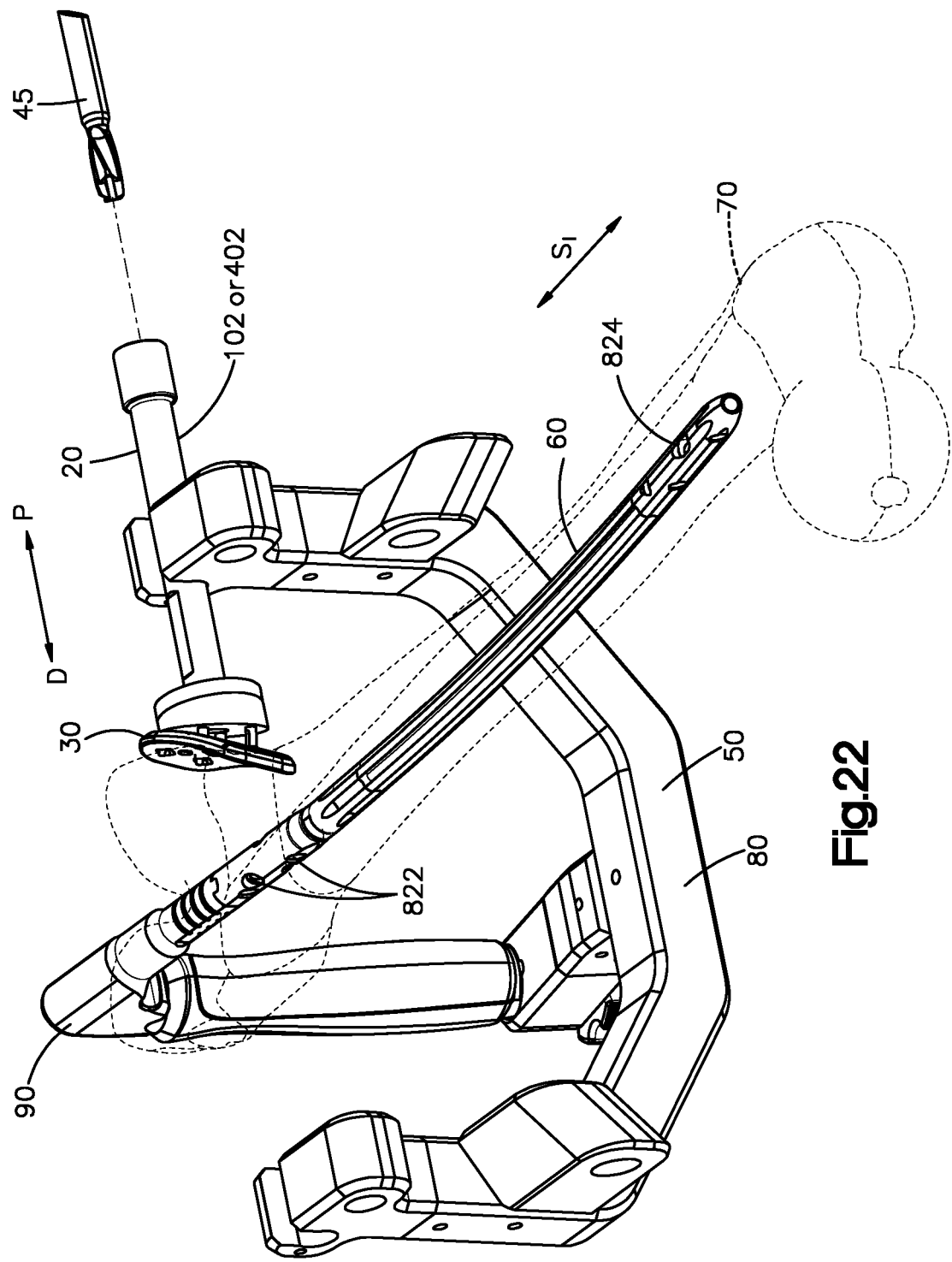
FIG. 22 shows a perspective view of the system of FIG. 21 with the variable-angle bone-plate placement tool supported by the aiming guide and receiving a drill bit to prepare the bone for receipt of a bone anchor.
Figure 23:
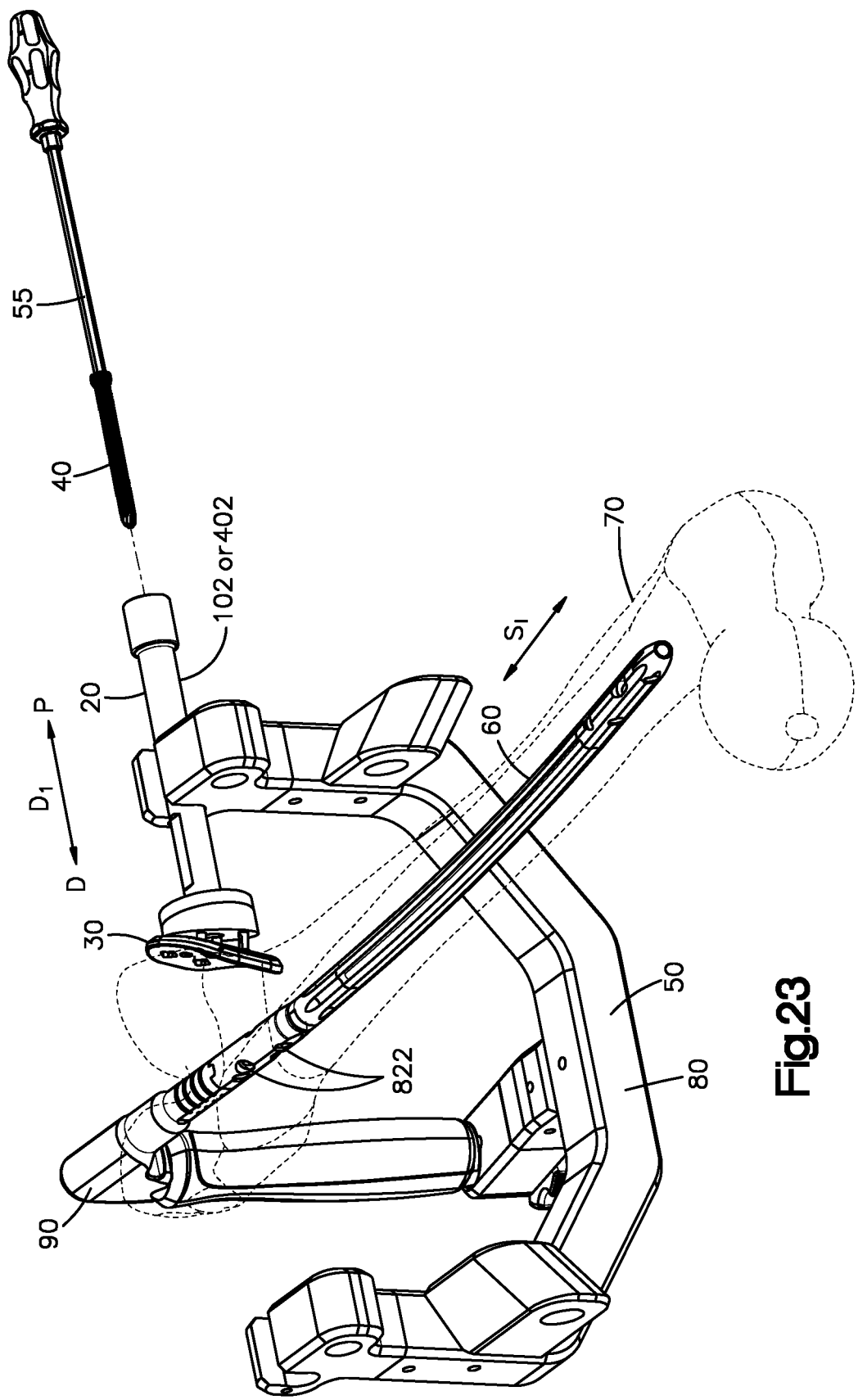
FIG. 23 shows a perspective view of the system of FIG. 21 with the variable-angle bone-plate placement tool receiving a first bone anchor inserted with a screw driver.
Figure 24:
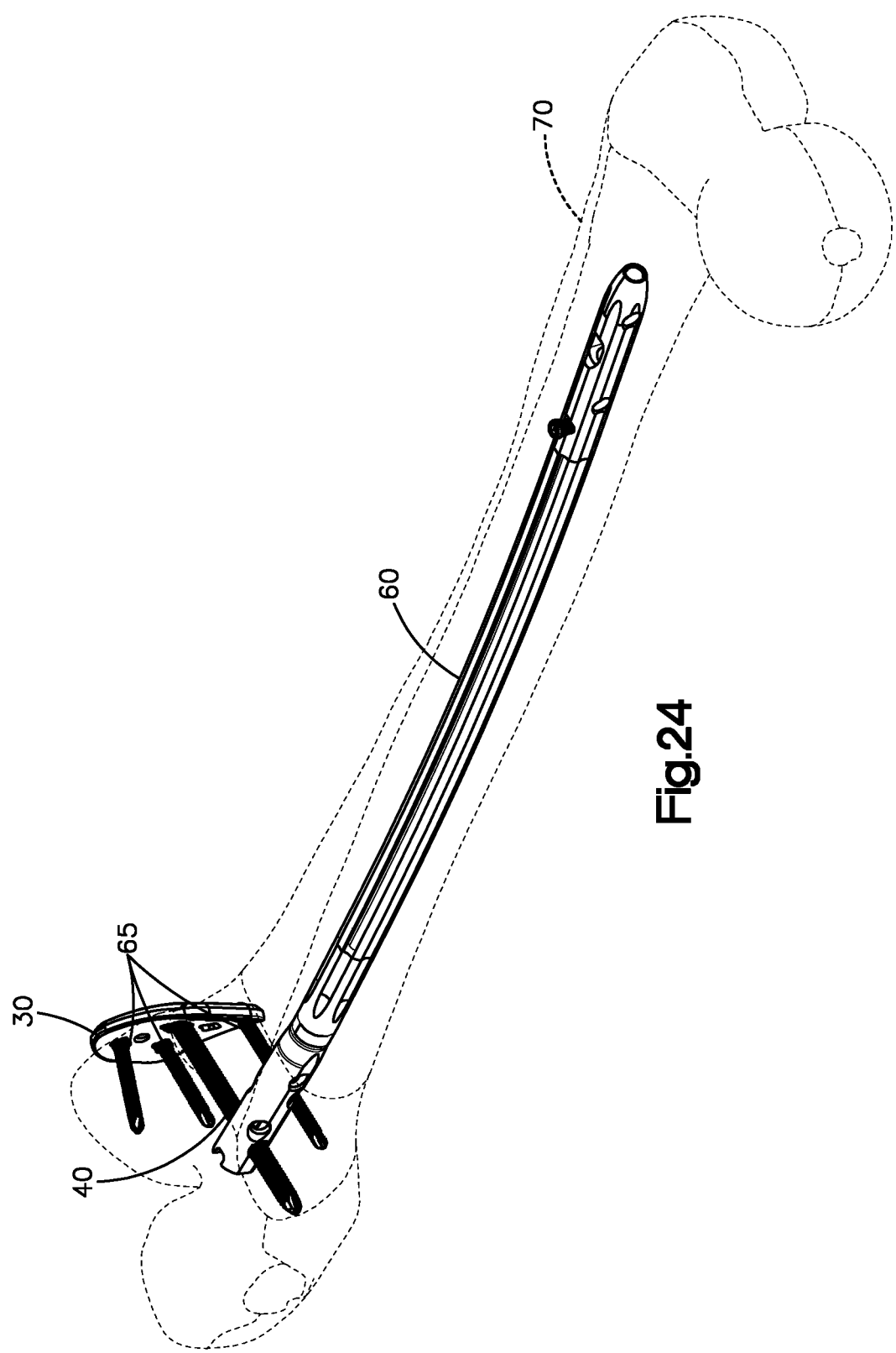
FIG. 24 shows a perspective view of the bone plate of the system of FIGS. 21-23 secured to the intramedullary nail via the first bone anchor and to the bone via a plurality of additional bone anchors.

In FIG. 22, a drill bit 45 is inserted through the passageway (e.g., 108 or 408) of the bone-plate placement tool 20 and into the bone 70 so as to bore a hole in the bone that extends to the bone-anchor aperture 822 of the intramedullary nail 60. In FIG. 23, a bone anchor 40 such as a bone screw is inserted by a driving instrument 55, such as a screw driver or drill, through the passageway (e.g., 108 or 408) in the guide shaft (e.g., 102 or 402), through the bone-anchor aperture (e.g., 216 in FIG. 10 or 516 in FIG. 17) in the bone plate 30, and into one of the bone-anchor apertures 822 of the intramedullary nail 60 such that the bone anchor 40 attaches the bone plate 30 and the intramedullary nail 60. In FIG. 24, at least one additional bone anchor 65 is inserted through an additional bone-anchor aperture (e.g., 218 in FIG. 10 or 418 in FIG. 17) in the bone plate and into the bone so as to further secure the bone plate to the bone. Further, the bone-plate placement tool 20 is removed from the bone plate 30, and the aiming assembly 50 is removed from the intramedullary nail 60.

Note that the steps of the method need not be performed in the order described. For example, the bone plate 30 can be fastened to the bone-plate placement tool 20 before or after the bone-plate placement tool 20 is coupled to the aiming assembly 50. As another example, the at least one additional bone anchor 65 can be inserted to attach the bone plate 30 to the bone 70 before one or both of (i) the drill bit 45 bores the hole in the bone 70 and (ii) the bone plate 30 is attached to the intramedullary nail 60 via the bone anchor 40. In fact, the bone-plate placement tool 20 can be removed from the bone plate 30 before the bone anchor 40 is inserted through the bone plate 30 and into the intramedullary nail 60. Thus, the bone anchor 40 can be inserted without passing the bone anchor 40 through the passageway (e.g., 108 or 408) in the guide shaft (e.g., 102 or 402).

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

It should be noted that the illustrations and descriptions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should further be appreciated that the various alternative embodiments described above with respect to one illustrated embodiment can apply to all embodiments as described herein, unless otherwise indicated.

Unless explicitly stated otherwise, each numerical value and range should be interpreted as being approximate as if the word "about" or "approximately" preceded the value or range.

It should be understood that the steps of exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

We claim:

1. A bone-plate placement tool, comprising:
    a guide shaft that defines a bore extending therethrough along a shaft longitudinal axis; and
    a plate holder that is configured to releasably couple to a bone plate, and the plate holder is further coupled to the guide shaft such that the plate holder is configured to angulate relative to the shaft longitudinal axis along a range of angles, the plate holder defining a bore extending therethrough,
    wherein the bores of the guide shall and the plate holder combine to define a passageway that extends through the bone-plate placement tool as the plate holder angulates with respect to the shaft longitudinal axis along the range of angles, the passageway configured to guide at least one of a drill bit and a bone anchor through the bone-plate placement tool and into an aperture in the bone plate when the plate holder is coupled to the hone plate; and
    an aiming assembly configured to support the bone-plate placement tool such that, when the aiming assembly is coupled to an intramedullary nail, the aiming assembly aligns the shaft longitudinal axis of the bore with a bone-anchor aperture that extends into an intramedullary nail attached to the aiming assembly such that the bore is configured to receive at least one of a drill bit and a bone anchor through the bore and towards the bone-anchor aperture of the intramedullary nail.

2. The bone-plate placement tool of claim 1, wherein the plate holder is configured to angulate polyaxially relative to the guide shaft, and the plate holder is configured to couple to the bone plate such that the bone plate is positionally fixed relative to the plate holder and the bone plate angulates polyaxially with the plate holder relative to the guide shaft.

3. The bone-plate placement tool of claim 1, wherein the guide shaft and plate holder are coupled to one another at a joint.

4. The bone-plate placement tool of claim 3, wherein the joint is a spherical joint.

5. The bone-plate placement tool of claim 3, wherein the joint comprises a socket, and a head received in the socket.

6. The bone-plate placement tool of claim 5, wherein the guide shaft includes the head, and the plate holder defines the socket.

7. The bone-plate placement tool of claim 6, wherein the head has an outer curved surface, and the plate holder has an inner curved surface that defines the socket, wherein the inner and outer curved surfaces are at least partially spherical and are configured to translate along one another when the head is angulated in the socket.

8. The bone-plate placement tool of claim 7, wherein the outer curved surface is convex and the inner curved surface is concave.

9. The bone-plate placement tool of claim 6, wherein the guide shaft has guide shaft body, the guide shaft body having a shaft proximal end and a shaft distal end that are spaced from one another along a first direction, and the head extends from the shaft distal end.

10. The bone-plate placement tool of claim 9, wherein the plate holder has a proximal holder end and a distal holder end that oppose one another, and the plate holder defines a proximal opening that extends into a proximal holder end surface, the proximal holder opening sized and configured to receive the guide shaft such that the guide shaft extends out of the proximal holder opening along a proximal direction when the head is received in the socket.

11. The bone-plate placement tool of claim 6, wherein the head is integrally formed with the shaft distal end.

12. The bone-plate placement tool of claim 6, wherein the head is removably attached to the shaft distal end.

13. The bone-plate placement tool of claim 1, comprising at least one bone-plate fastener configured to releasably fasten a bone plate to the plate.

14. The bone-plate placement tool of claim 13, wherein the at least one fastener includes at least one projection that extends from the plate holder, the at least one projection configured to engage a corresponding recess in the bone plate so as to secure the plate holder and the hone plate to one another.

15. A bone-plate placement system, comprising:
the bone-plate placement tool of claim 1, wherein the bore of the guide shaft extends along a shaft longitudinal axis; and
a bone plate defining a bone-anchor aperture that extends therethrough such that, when the bone plate is fastened to the plate holder, the shaft longitudinal axis aligns with the bone-anchor aperture so as to receive at least one of a drill bit and a bone anchor through the bore of the guide shaft and into the bone-anchor aperture.

* * * * *